US011542291B2

(12) United States Patent
Ziegler et al.

(10) Patent No.: US 11,542,291 B2
(45) Date of Patent: Jan. 3, 2023

(54) COMPOUNDS, COMPOSITIONS, AND METHODS FOR COLORING EDIBLE MATERIALS

(71) Applicant: The Penn State Research Foundation, University Park, University Park, PA (US)

(72) Inventors: Gregory Ray Ziegler, State College, PA (US); Joshua David Lambert, State College, PA (US); Emmanuel Hatzakis, Columbus, OH (US); Eugene P. Mazzola, Vienna, VA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 16/512,445

(22) Filed: Jul. 16, 2019

(65) Prior Publication Data
US 2020/0017538 A1    Jan. 16, 2020

Related U.S. Application Data

(60) Provisional application No. 62/698,423, filed on Jul. 16, 2018.

(51) Int. Cl.
| | |
|---|---|
| *C07H 15/24* | (2006.01) |
| *C07D 305/10* | (2006.01) |
| *C07H 15/26* | (2006.01) |
| *C07C 59/82* | (2006.01) |

(52) U.S. Cl.
CPC .............. *C07H 15/24* (2013.01); *C07C 59/82* (2013.01); *C07D 305/10* (2013.01); *C07H 15/26* (2013.01); *C07C 2603/30* (2017.05)

(58) Field of Classification Search
CPC .......... C07H 15/24; C07H 15/26; C07C 59/82
See application file for complete search history.

(56) References Cited

U.S. PATENT DOCUMENTS

| | | | | |
|---|---|---|---|---|
| 2,550,254 | A * | 4/1951 | Jensen | A61K 36/54 424/765 |
| 3,393,208 | A | 7/1968 | Plostnieks | |
| 4,172,949 | A | 10/1979 | Dunn | |
| 8,658,237 | B2 | 2/2014 | Fukui | |
| 8,784,853 | B2 | 7/2014 | Wagner | |
| 2007/0178216 | A1 | 8/2007 | Kandaswami | |
| 2017/0121363 | A1 * | 5/2017 | Ziegler | C09B 61/00 |

FOREIGN PATENT DOCUMENTS

| | | |
|---|---|---|
| DE | 2148513 A1 | 4/1972 |
| EP | 1663931 | 6/2006 |
| WO | 2005021479 | 3/2005 |
| WO | 2010134595 | 11/2010 |
| WO | 2011048011 | 4/2011 |
| WO | 2017079564 | 5/2017 |

OTHER PUBLICATIONS

Yamamoto (Bulletin of The Chemical Society of Japan; vol. 50(8), 1964-1968 (1977).*
Cheung et al., "Aromatic Saddles Containing Two Heptagons", 2015, J Am Chem Soc, 137:3910-3914.
Dabas et al., "A Colored Avocado Seed Extract as a PotentialNatural Colorant", 2011. J. Food Sci 76:C1335-1341.
Dabas, 2012, Ph.D. Thesis, "A Colored Avocado Seed Extract With Antioxidant, Anti-Carcinogenic and Anti-Inflammatory Effects" The Pennsylvania State University; pp. 1-142.
Das et al., "Dyeing of Wool and Silk with Tea", International Journal of Tea Science, 2005, 4:17-25.
Deniz Arican et al. "Syntheses of 3,4-Benzotropolones by Ring-Closing Metatheses", 2013, Organic Letters 15:2582-2585.
Evans et al., "Pigment production from immobilizedMonascus sp utilizing polymeric resin adsorption", 1984, Appl Environ Microbiol 47:1323-1326.
Ginda et al., "Salviolone, a cytotoxic bisnorditerpene with a benzotropolone chromophore from a Chinese drug dan-shen (*Salvia miltiorrhiza*)", 1988, Tetrahedron 29:4603-4606.
Horner et al., "Zur elektrophilen Substitution des Benzocyclobutens", 1960, Eur J Inorg Chem 93:1774-1781.
Kahn, Varda. "Characterization of Starch Isolated from Avocado Seeds", 1987, J Food Sci 52:1646-1648.
Kerschensteiner et al., "Crocipodin, a benzotropolone pigment from the mushroom Leccinum crocipodium (Boletales)", 2011, Tetrahedron 67:1536-1539.
Korankye, 2010, M.A. Thesis, "Extraction and Application of Plant Dyes to Serve as Colourants for Food and Textiles" Kwame Nkrumah University of Science and Technology, Kumasi pp. 1-92.
Lea, Andrew. "Flavor, Color, and Stability in Fruit Products: The Effect of Polyphenols", 1992, Chapter in Plant Polyphenols, pp. 827-847.
Leite et al., "Chemical composition, toxicity and larvicidal and antifungal activities of Persea americana (avocado) seed extracts", 2009, Rev Soc Bras Med Trop 42:110-113.
Menet et al., "Analysis of Theaflavins and Thearubigins from Black Tea Extract by MALDI-TOF Mass Spectrometry", 2004, J Agric Food Chem 52(9):2455-2461.
R. Munday et al. "Synthesis of Compounds Related to Cyclohepta[def-]fluorene", 1969, Journal of the Chemical Society C: Organic, 10:1427-1434.
Remias et al., "Characterization of an UV- and VIS-absorbing, purpurogallin-derived secondary pigment new to algae and highly abundant in Mesotaenium berggrenii (Zygnematophyceae, Chlorophyta), an extremophyte living on glaciers", 2012, FEMS Microbiol Ecol 79:638-648.
Shin-Ichi Naya et al. "Synthesis, Properties, and Oxidizing Ability of Areno-Annulated 1,3-Dimethyl-10-phenylcyclohepta[4,5]pyrrolo[2,3-d]pyrimidine-2,4(1,3 H)-dionylium Ions", 2006, Journal of Organic Chemistry 71:176-184.

(Continued)

*Primary Examiner* — Pancham Bakshi
(74) *Attorney, Agent, or Firm* — Buchanan Ingersoll & Rooney PC

(57) ABSTRACT

The present invention provides compounds isolated from avocado seeds for use as a natural colorant in edible materials. The compounds of the invention are useful for coloring edible materials red, orange, or yellow. The invention also provides compositions and methods for coloring edible materials to a desired color such as red, orange, or yellow.

3 Claims, 19 Drawing Sheets

(56) References Cited

OTHER PUBLICATIONS

Tanaka et al., Proceedings of the 2001 International Conference on 0-cha (tea) Culture and Science, 2001, Session II, pp. 276-279.
Weatherby et al., "Chemical Composition of Avocado Seed", 1931, Industrial & Engineering Chemistry 23:1421-1423.
PubChem CID 12322926, Feb. 7, 2007, pp. 1-5.
PubChem CID 11050, Mar. 26, 2005, pp. 1-20.
Murata, I., et al., Cyclohepta[cd]phenalen-6-on, Angew Chem., 1974, vol. 86, No. 23, pp. 861-862.
Pascal, Jr., R.A. et al., Synthesis and Structure of 1,7-Dichlorodibenzo[ef,kl]heptalene-4,10-dione, a Saddle-Shaped Polycyclic Aromatic Compound, Tetrahedron Letters, 1992, vol. 33, No. 1, pp. 13-16.
European Search Report for EP 19838626.0-1110, dated Mar. 7, 2022.
Maulik, S.R., et al., Concurrent dyeing and finishing of cotton with natural colour and citric acid in the presence of $NaH_2PO_4$ as catalyst under thermal treatment, Journal of the Textile Institute, 2011, vol. 102, No. 6, pp. 491-499.
European Search Report for EP 16863047.3, dated May 11, 2022.
European Search Report for EP 19838626.0-1110, dated Jun. 9, 2022.

\* cited by examiner

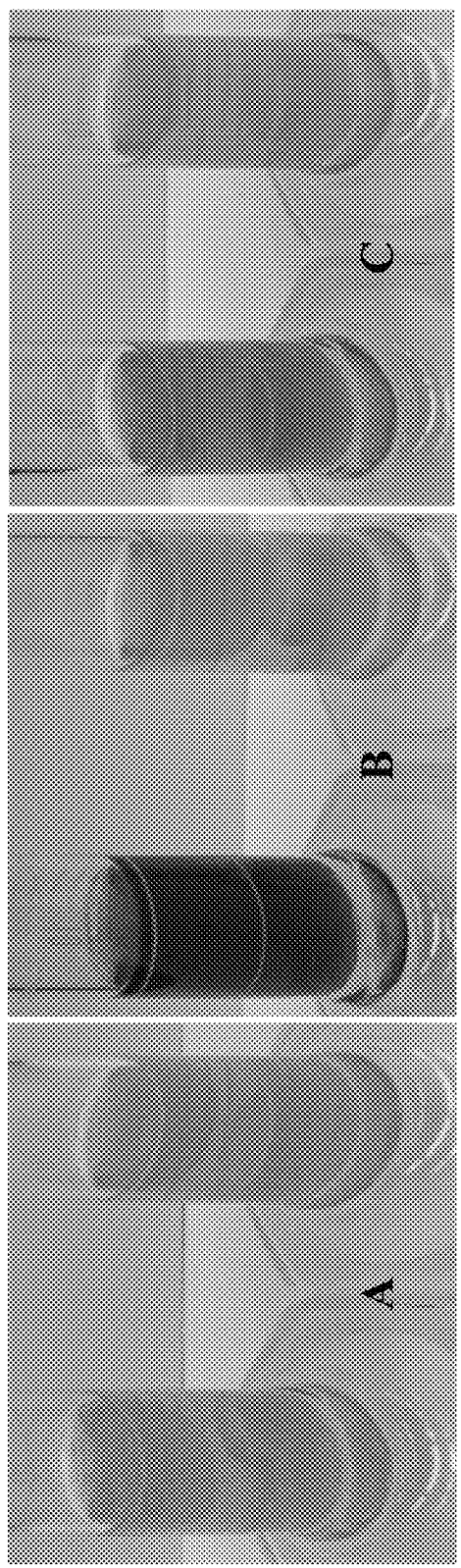
Figure 2A-C

COMPOUNDS, COMPOSITIONS, AND METHODS FOR COLORING EDIBLE MATERIALS

CROSS-REFERENCE TO RELATED APPLICATIONS

The present application claims priority to U.S. Provisional Application Ser. No. 62/698,423, filed on Jul. 16, 2018, which is incorporated by reference herein in its entirety.

REFERENCE TO GOVERNMENT GRANT

This invention was made with government support under Grant No. PEN04565, awarded by The United States Department of Agriculture Hatch Act and under Grant No. AT004678, awarded by the National Institutes of Health. The Government has certain rights in the invention.

BACKGROUND OF THE INVENTION

Color has a direct and significant connection with human sensory perception of foods as the sense of sight plays a critical role in food choice and safety. Edible colorants are a category of food additives that are extensively used by the food, drug and cosmetic industries. The United States Food and Drug Administration (FDA) divides food colorants into two categories based on perceived risk: certified colors (commonly referred to as "synthetic" or "artificial"), and those exempt from certification (commonly referred to as "natural"). The former are subjected to extensive pre-market safety testing and in the US are assigned Food, Drug and Cosmetic (FD&C) numbers. The latter typically do not require extensive pre-market safety testing and are considered safe based on their general historical use in foods. A natural colorant can be defined as any pigment which is produced by any organism, such as plant, animal, fungi or microorganism (Luning et al., 2008, Food Colorants: Chemical and Functional Properties (p. 557). Boca Raton, Fla.: CRC Press, Taylor & Francis Group). A natural food colorant can be either extracted from its natural source (e.g. safranal from saffron) or, after discovery, can be chemically synthesized (e.g. β-carotene). The latter is referred to as "nature identical."

The global market for food colors is expected to reach US $3.75 billion by 2022, with North America dominating the market, followed closely by Europe (Rizvi et al., 2016, Food Colors Market, Global Forecast to 2022, retrieved from https://www.marketsandmarkets.com/Market-Reports/food-colors-market-36725323.html). Synthetic food colorants have several advantages compared to natural pigments including excellent heat, light, and oxygen stability, vibrancy, and lower costs of production. For these reasons they are commonly used in many popular formulated foods including confections, baked goods, and soft drinks.

While some studies have suggested potential negative health consequences related to consumption of synthetic food colors including potential carcinogenicity, allergic reactions, and neurological effects, data are inconsistent (Amin et al., 2010, Food and Chemical Toxicology, 48:2994-2999; Feketea et al., 2017, Food Chemistry, 230: 578-588; McCann et al., 2007, The Lancet, 370:1560-1567; Sasaki et al., 2002, Mutation Research/Genetic Toxicology and Environmental Mutagenesis, 519:103-119). Consumer demand, however, has placed an emphasis on health and wellness, safety, and environmentally-friendly processes, and consumers are increasingly concerned by the perceived negative health risks associated with synthetic food colors. Consumer demand for so-called "clean label" products has caused a shift in the global food colors market; demand for natural food colors has seen significant growth, outstripping sales of synthetic colors in 2016, with particular interest in compounds responsible for yellow, orange, red, and pink colors (Rizvi et al., 2016, Food Colors Market, Global Forecast to 2022, retrieved from https://www.marketsandmarkets.com/Market-Reports/food-colors-market-36725323.html) because they are involved in the majority of applications, although blue and green colorants are also important due to the difficulty in obtaining these hues in food products.

Polyphenol oxidases (PPOs) are enzymes found almost universally in all varieties of organisms including bacteria, mammals, and plants, and are responsible for the production of brown and yellow-red pigments. PPO has a di-nuclear copper active site which exerts these effects through the ability to bind an external diphenol molecule and oxidize it to an O-quinone that is released with a water molecule ("EC 1.14.18.1" 2018). These reactive O-quinones are then converted, via non-enzymatic pathways (Dogan et al., 2006, Process Biochemistry, 41:2379-2385), to red, brown, and black pigments that are usually viewed as undesirable (e.g. the browning of apples and bananas). There are some situations in which PPO contributes to the development of the desirable, characteristic pigments associated with foods, as in the case of benzotropolone-containing theaflavins in black tea (Menet et al., 2004, Journal of Agricultural and Food Chemistry, 52:2455-2461). Benzotropolones contain the characteristic seven-membered tropolone ring attached to a six-membered aromatic ring. Benzotropolones are generally yellow, orange, red or brown in color and, in addition to black tea, have been found in edible mushrooms, Chinese sage (*Salvia miltiorrhiza*), and Snow algeae (*Mesotaenium berggrenii*) (Ginda et al., 1988, Tetrahedron Letters, 29:4603-4606; Kerschensteiner et al., 2011, Tetrahedron, 67:1536-1539; Menet et al., 2004, Journal of Agricultural and Food Chemistry, 52:2455-2461; Remias et al, 2012, FEMS Microbiology Ecology, 79:638-648).

It has previously been reported that when the seeds of avocados (Species: *Persea americana*; Family: Lauraceae) are crushed and exposed to oxygen, a vibrant and stable orange pigment develops in a PPO-dependent reaction (Dabas et al., 2011, Journal of Food Science, 76:C1335-C1341). Although there are historical reports of the use of a colored exudate from avocado seeds as an indelible ink by Spanish conquistadors, the use of this extract as a food color has not been reported, nor have the major pigments been previously identified (Morton et al., 1987, Fruits of Warm Climates (J. F. Morton, Ed.), Miami, Fla.). Although the observed similarities to theaflavins (e.g. the development of an orange pigment in a PPO-dependent reaction and the presence of similar biosynthetic precursors in the seed) suggests a benzotropolone-like moiety, further studies are needed to determine the identity of the compounds responsible for the orange color, and their colorant characteristics in various systems.

Thus, there is a need in the art for novel natural colorants. The present invention fulfills this unmet need.

SUMMARY OF THE INVENTION

In one aspect, the invention provides a compound of general formula (1):

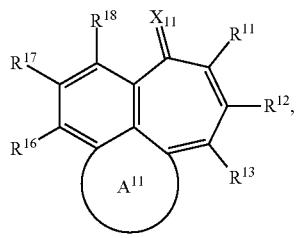

(I)

wherein in general formula (1), $R^{11}$-$R^{13}$ and $R^{16}$-$R^{18}$ are each independently selected from the group consisting of hydrogen, hydroxyl, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, $(C(R^{19}R^{110}))_n$, $(C(R^{19}R^{110}))_nOR^{111}$, $(C(R\ R^{19}R^{110}))_n(NR^{122})R^{121}$, $N(R^{19}R^{110})$, and $OR^{19}$, wherein any of $R^{11}$-$R^{13}$ and $R^{16}$-$R^{18}$ are optionally joined to form a ring, wherein the ring is optionally substituted;

each occurrence $R^{19}$ and $R^{110}$ is independently selected from the group consisting of hydrogen, an alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein $R^9$ and $R^{10}$ are optionally joined to form a ring;

each occurrence $R^{11}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

each occurrence $R^{12}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl;

each occurrence of n is independently an integer from 0 to 10;

$X^{11}$ is selected from the group consisting of O, NH, and S; and $A^{11}$ is selected from the group consisting of an optionally substituted 3 to 10 membered monocyclic cycloalkyl, an optionally substituted 3 to 10 membered bicyclic cycloalkyl, an optionally substituted 3 to 10 membered monocyclic heterocyclyl, an optionally substituted 3 to 10 membered bicyclic heterocyclyl, an optionally substituted 3 to 10 membered aryl, and an optionally substituted 3 to 10 membered heteroaryl.

In one embodiment, the compound of general formula (1) is represented by general formula (2):

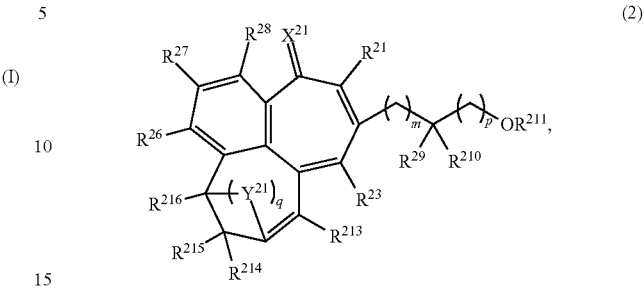

(2)

wherein in general formula (2), $R^{21}$, $R^{23}$, $R^{26}$-$R^{28}$, and $R^{213}$-$R^{216}$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein any of $R^{21}$, $R^{23}$, $R^{26}$-$R^{28}$, and $R^{213}$-$R^{216}$ are optionally joined to form a ring, wherein the ring is optionally substituted;

$R^{29}$ and $R^{210}$ are each independently selected from the group consisting of hydrogen, an alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, and $C(=O)R^{211}$, wherein $R^{29}$ and $R^{210}$ are optionally joined to form a ring;

each occurrence $R^{211}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

Y is selected from the group consisting of $C(R^{217}R^{18})$, $NR^{217}$, $SR^{217}$, and $OR^{217}$;

$R^{217}$ and $R^{218}$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, halogen, and hydroxyl;

m is an integer from 0 to 11;

p is an integer from 0 to 5;

q is an integer from 1 to 5; and $X^{21}$ is selected from the group consisting of O, NH, and S.

In one embodiment, the compound is selected from the group consisting of

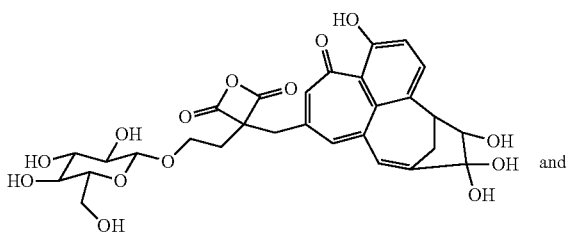

and

-continued

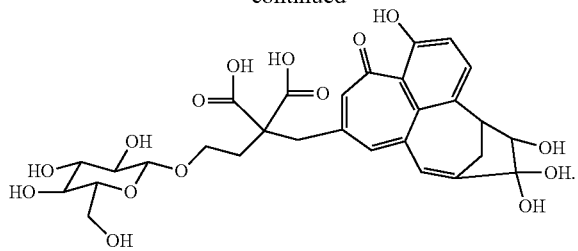

In one embodiment, the compound is selected from the group consisting of

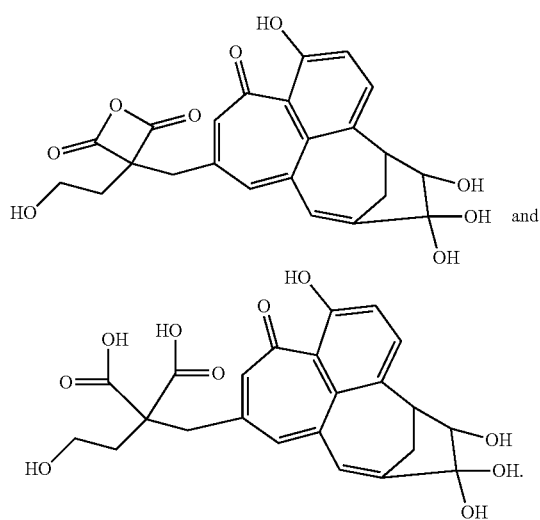

In one embodiment the compound forms a dimer.

In one embodiment, the compound has a hue selected from the group consisting of yellow, orange, and red.

In one embodiment, the invention includes a composition comprising a compound of the invention and one or more uncolored compounds. In one embodiment, the invention includes a composition comprising a compound of the invention and one or more colored compounds.

In another aspect, the invention provides an edible material comprising a compound of the invention. In one embodiment, the edible material has a hue selected from the group consisting of orange, red, and yellow.

In another aspect, the invention provides a method of coloring an edible material, the method comprising adding to the edible material a compound of the invention.

In another aspect, the invention provides a compound isolated by the process comprising the steps of: obtaining a seed of Persea americana; blending the seed; isolating supernatant from the blended seed; filtering the supernatant; lyophilizing the filtered supernatant; performing a first purification by flash chromatography to yield a first semi-pure substance; performing a second purification by reverse phase HPLC to obtain a crude substance; and performing a third purification by reverse phase HPLC to obtain to obtain a purified compound.

In one embodiment, the second purification is a C18 reverse phase HPLC purification. In one embodiment, the performing the second purification comprises introducing the semi-pure substance to a C18 column, and eluting with a gradient of water, acetonitrile and optionally acetic acid.

In one embodiment, the third purification is an Ultra Aromax® reverse phase HPLC purification. In one embodiment, the performing the third purification comprises introducing the crude substance to an Ultra Aromax® column, and eluting with a gradient of water, alcohol and optionally acetic acid. In one embodiment, the alcohol is methanol, ethanol, isopropanol, butanol, or combinations thereof.

In one embodiment, the step of performing a first purification comprises the step of loading the filtered supernatant onto an XAD7-HP resin. In one aspect, the invention provides a method of imparting a color to a substrate. In one embodiment the method comprises applying a compound of the invention to the substrate. In one embodiment, color is selected from the group consisting of red, yellow, and orange. In one embodiment, the substrate is an edible material. In one embodiment, the substrate is a cosmetic or personal care product. In one embodiment the substrate is a home care product.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 2, comprising FIG. 2A through FIG. 2C, depicts the color of semi-pure perseorangin at different pH levels (left) versus control (right). FIG. 2A depicts pretreatment at a pH of 3.32. FIG. 2B depicts base treatment to pH 12.32. FIG. 2C depicts re-acidification to pH 1.59.

FIG. 3, comprising FIG. 3A depicts positive mode. FIG. 3B depicts negative mode.

FIG. 13, comprising FIG. 13A depicts the analysis of CASE by HPLC-UV/Vis, the eluent was monitored at λ=280 (1), 325 (2), and 445 nm (3). Perseorangin (PO) had a retention time of 24.7 min. LC-MS metabolomics was performed in both the positive and negative ionization modes. FIG. 13B depicts PCA loadings and score plots (insets) for CASE and uncolored extract in the positive ion mode.

FIG. 15, comprising FIG. 15A depicts the $^1$H NMR analysis performed at 500 MHz. FIG. 15B depicts the $^{13}$C NMR analysis performed at 125.77 MHz. The assignments of the labeled signals are presented in Table 2. For analysis, the compound was dissolved in DMSO-d$_6$.

DETAILED DESCRIPTION OF THE INVENTION

Figure 1:
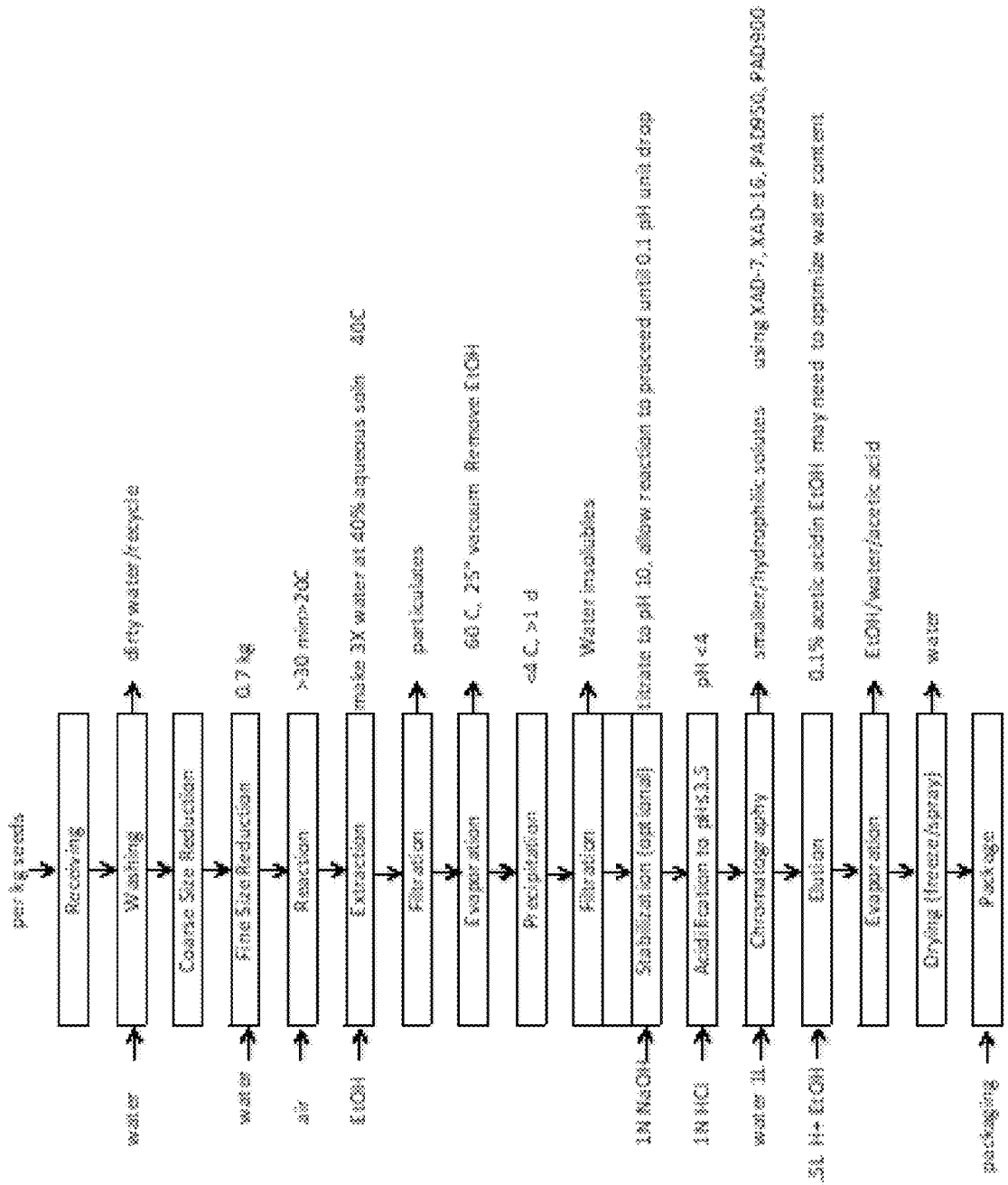
FIG. 1 depicts a method for isolating for isolating compounds from avocado seed extract.

This invention relates to the unexpected identification of novel compounds isolated from colored avocado seed extract and their utility as source of natural colorants. In some aspects, the compounds may be used as an orange colorant. In another embodiment, the compounds may be used as a yellow colorant. In yet another embodiment, the compounds may be used as a red colorant. However, the invention should not be limited to only these colors or shades. Rather, the invention includes any desired color or shade that is associated with one or more of hues yellow, orange, and red. In one embodiment, the invention includes any color or shade in the spectrum for yellow, orange, and red. In one embodiment, the invention includes any color or shade that contains one or more of yellow, orange, and red.

Definitions

Unless defined otherwise, all technical and scientific terms used herein have the same meaning as commonly understood by one of ordinary skill in the art to which this invention belongs. Methods and materials similar or equivalent to those described herein can be used in the practice or testing of the present invention.

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "benzotropolone" refers to a seven-membered tropolone ring attached to a six-membered aromatic ring.

As used herein, the term "benzotropone" refers to a seven-membered tropone ring attached to a six-membered aromatic ring.

As used herein, the term colored avocado seed extract (CASE), perseorangin, F12, and Avocolor are used to describe a composition for coloring food which is isolated from an Avocado seed using a method of the invention. In one embodiment, CASE, perseorangin, F12, and Avocolor comprise a compound of the invention.

In one embodiment, compounds of the invention contain saccharides. "Saccharides" as used herein, include, but are not limited to aldose or ketose pentosyl or hexosyl sugars selected from the group consisting of D- and L-enantiomers of ribose, glucose, galactose, mannose, arabinose, allose, altrose, gulose, idose, talose and their substituted derivatives. In one embodiment, the subject sugar comprises an aldose pentosyl or hexosyl sugar selected from ribose, glucose, galactose, glucosamine, galactosamine, N-acetylglucosamine, N-acetylgalactosamine, N-acetyl ribosamine, xylose, mannose and arabinose.

"Di-saccharide", when used in regard to the subject sugar residue, is intended to mean a polymeric assemblage of 2 sugar residues. Representative examples of disaccharides include homo-polymeric (e.g., maltose and cellobiose) and hetero-polymeric (e.g., lactose and sucrose) assemblages of sugars as set forth supra.

"Tri-saccharide", when used in regard to the subject sugar residue, is intended to mean a polymeric assemblage of 3 sugar residues.

"Polysaccharide", when used in regard to the subject sugar residue, is intended to mean a polymeric assemblage of 3 or more sugar residues.

An "effective amount" of a delivery vehicle is that amount sufficient to effectively bind or deliver a compound.

The term "compound," as used herein, unless otherwise indicated, refers to any specific chemical compound disclosed herein. In one embodiment, the term also refers to stereoisomers and/or optical isomers (including racemic mixtures) or enantiomerically enriched mixtures of disclosed compounds.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. In one embodiment an alkyl is ($C_1$-$C_6$) alkyl, particularly ethyl, methyl, isopropyl, isobutyl, n-pentyl, n-hexyl and cyclopropylmethyl.

As used herein, the term "alkenyl," employed alone or in combination with other terms, means, unless otherwise stated, a stable mono-unsaturated, di-unsaturated, or poly-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene may be exemplified by —CH$_2$—CH=CH$_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C≡CH. The term "homopropargylic" refers to a group exemplified by —CH$_2$CH$_2$—C≡CH. The term "substituted propargylic" refers to a group exemplified by —CR$_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —CR$_2$CR$_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl cycloalkyl, alkenyl or alkynyl, as defined above, substituted by one, two or three substituents selected from the group consisting of halogen, —OH, alkoxy, —NH$_2$, —N(CH$_3$)$_2$, —C(=O), —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$, in some embodiments containing one or two substituents selected from halogen, —OH, alkoxy, —NH$_2$, trifluoromethyl, —N(CH$_3$)$_2$, and —C(=O)OH. In one embodiment, the substitutent is selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Examples are (C$_1$-C$_3$) alkoxy, particularly ethoxy and methoxy.

As used herein, the term "halo" or "halogen" alone or as part of another substituent means, unless otherwise stated, a fluorine, chlorine, bromine, or iodine atom. In one embodiment a halogen means fluorine, chlorine, or bromine. In one embodiment, the halogen is fluorine or chlorine.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

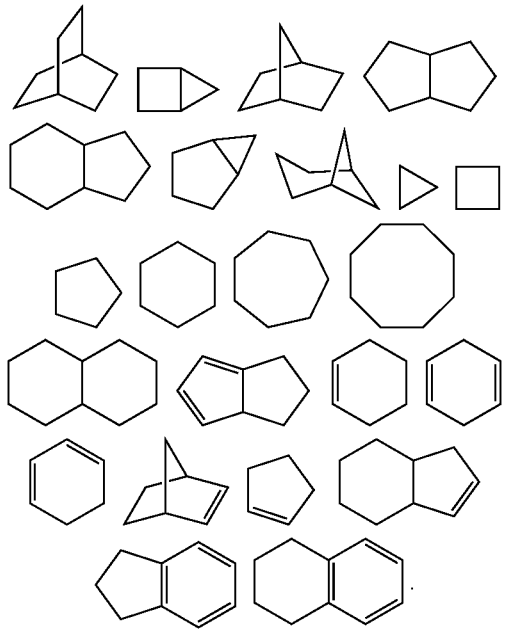

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbomane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine, and piperazine. Other non-limiting examples of heterocycloalkyl groups are:

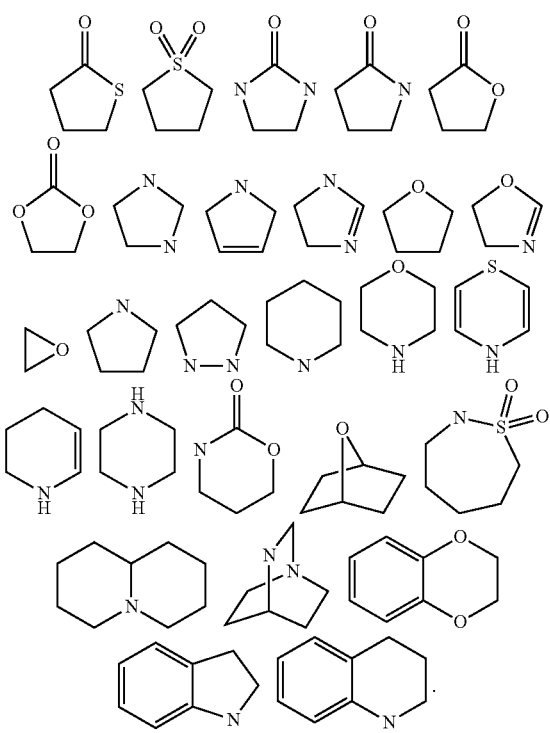

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracenyl, and naphthyl. Examples include phenyl and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. Examples include aryl-$CH_2$— and aryl-$CH(CH_3)$—. The term "substituted aryl-($C_1$-$C_3$)alkyl" means an aryl-($C_1$-$C_3$) alkyl functional group in which the aryl group is substituted. In one embodiment the aryl-($C_1$-$C_3$)alkyl" is a substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. In one embodiment, the "heteroaryl-($C_1$-$C_3$)alkyl" is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. In one embodiment, the term "substituted heteroaryl-($C_1$-$C_3$)alkyl" is substituted heteroaryl-($CH_2$)—.

As used herein, the term "heteroaryl" or "heteroaromatic" refers to a heterocycle having aromatic character. A polycyclic heteroaryl may include one or more rings that are partially saturated. Examples include the following moieties:

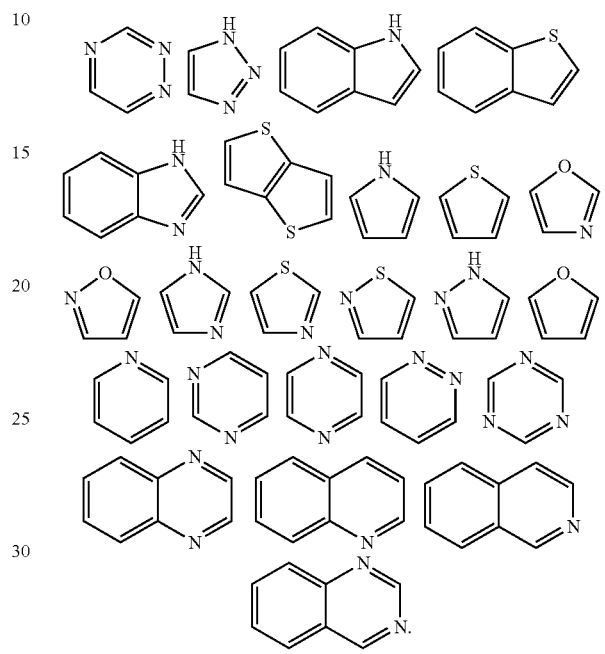

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention is partly based on the successful production of a semi-pure extract containing a compound of interest that has been tested in food applications including beverages, confectionery, dry mixes, bake goods, and the like. Accordingly, the invention provides compositions and methods of using a compound as a natural food colorant. In another embodiment, the compound of the invention can be used in cosmetic settings. In one embodiment, the compound of the invention provides an advantage to existing food colorants in the art. For example, the compound of the invention is significantly more stable to heat, light, and oxygen, more vibrant, and less toxic.

Compounds

The compounds of the present invention may be synthesized using techniques well-known in the art of organic synthesis. The starting materials and intermediates required for the synthesis may be obtained from commercial sources or synthesized according to methods known to those skilled in the art.

Alternatively, the compounds of the present invention may be isolated from avocado seed extract. Thus, the present invention provides a method for isolating compounds from avocado seed extract. In one embodiment, the method comprises blending avocado seeds, filtering the supernatant, lyophilizing the filtered supernatant, performing a first purification using flash chromatography, performing a second purification using an HPLC C18 column, eluting with a gradient of acetic acid and acetonitrile, performing a third purification using an HPLC Ultra Aromax column, eluting with a gradient of acetic acid and methanol, and obtaining an isolated compound.

In one embodiment, the invention is a benzotropone or a benzotropone derivative. In one embodiment, the benzotropone is substituted with a sugar group. In one embodiment, the benzotropone is substituted with an alkoxy-sugar group. In one embodiment, the benzotropone is substituted with a monosaccharide. In one embodiment, the benzotropone is substituted with a disaccharide. In one embodiment, the benzotropone is substituted with a trisaccharide.

In one embodiment, the invention is a compound of general formula (1):

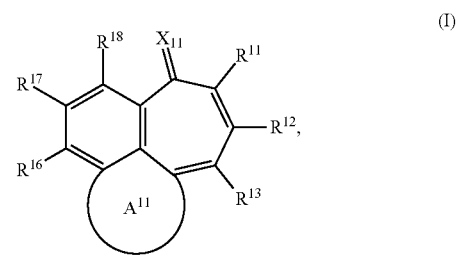

wherein in general formula (1),

R$^{11}$-R$^{13}$ and R$^{16}$-R$^{18}$ are each independently selected from the group consisting of hydrogen, hydroxyl, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, (C(R$^{19}$R$^{110}$))$_n$, (C(R$^{19}$R$^{110}$))$_n$OR$^{111}$, (C(R R$^{19}$R$^{110}$))$_n$(NR$^{122}$)R$^{121}$, N(R$^{19}$R$^{110}$), and OR$^{19}$, wherein any of R$^{11}$-R$^{13}$ and R$^{16}$-R$^{18}$ are optionally joined to form a ring, wherein the ring is optionally substituted;

each occurrence R$^{19}$ and R$^{110}$ is independently selected from the group consisting of hydrogen, an alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein R$^9$ and R$^{10}$ are optionally joined to form a ring;

each occurrence R$^{11}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

each occurrence $R^{12}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl;

each occurrence of n is independently an integer from 0 to 10;

$X^{11}$ is selected from the group consisting of O, NH, and S; and $A^{11}$ is selected from the group consisting of an optionally substituted 3 to 10 membered monocyclic cycloalkyl, an optionally substituted 3 to 10 membered bicyclic cycloalkyl, an optionally substituted 3 to 10 membered monocyclic heterocyclyl, an optionally substituted 3 to 10 membered bicyclic heterocyclyl, an optionally substituted 3 to 10 membered aryl, and an optionally substituted 3 to 10 membered heteroaryl.

In one embodiment, $X^{11}$ is O.
In one embodiment, $R^{11}$, $R^{13}$, $R^{16}$, and $R^{17}$ are each hydrogen.
In one embodiment, $R^{18}$ is hydroxyl.
In one embodiment $R^{12}$ is $(C(R^{19}R^{110}))_n OR^{111}$.
In one embodiment, n is 4.
In one embodiment, $R^{19}$ and $R^{110}$ are each hydrogen.
In one embodiment, $R^{19}$ and $R^{110}$ are each C(=O)OH. In one embodiment $R^{19}$ and $R^{110}$ are joined to form a ring. In one embodiment, the ring comprises an O atom. In one embodiment, the ring comprises one or more carbonyls. In one embodiment, the ring is a 3, 4, or 5 membered ring.

In one embodiment, $R^{111}$ is a monosaccharide. In one embodiment, $R^{111}$ is glucose, fructose, or galactose.

In one embodiment, $A^{11}$ is an optionally substituted 3 to 10 membered dicyclic cycloalkyl. In one embodiment, $A^{11}$ is an optionally substituted bicyclononyl. In one embodiment, $A^{11}$ is an optionally substituted bicyclo[4.2.1]nonyl. In one embodiment, $A^{11}$ is an optionally substituted bicyclononenyl. In one embodiment, A is an optionally substituted bicyclo[4.2.1]nonenyl. In one embodiment, $A^{11}$ is substituted with at least one hydroxyl group. In one embodiment, $A^{11}$ is substituted with three hydroxyl groups.

In one embodiment, the compound of general formula (1) is a compound of general formula (2):

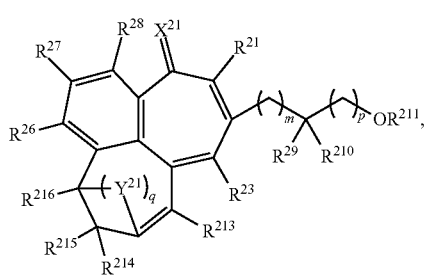

(2)

wherein in general formula (2),
$R^{21}$, $R^{23}$, $R^{26}$-$R^{28}$, and $R^{213}$-$R^{216}$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein any of $R^{21}$, $R^{23}$, $R^{26}$—$R^{28}$, and $R^{213}$-$R^{216}$ are optionally joined to form a ring, wherein the ring is optionally substituted;

$R^{29}$ and $R^{210}$ are each independently selected from the group consisting of hydrogen, an alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, and C(=O)$R^{211}$, wherein $R^{29}$ and $R^{210}$ are optionally joined to form a ring;

each occurrence $R^{211}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

$Y^{21}$ is selected from the group consisting of $C(R^{217}R^{18})$, $NR^{217}$, $SR^{217}$, and $OR^{217}$;

$R^{217}$ and $R^{218}$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, halogen, and hydroxyl;

m is an integer from 0 to 11;
p is an integer from 0 to 5;
q is an integer from 1 to 5; and
$X^{21}$ is selected from the group consisting of O, NH, and S.

In one embodiment, $X^{21}$ is O.
In one embodiment, $R^{21}$, $R^{23}$, $R^{26}$, $R^{27}$, $R^{213}$, $R^{214}$, $R^{215}$, and $R^{216}$ are each hydrogen.
In one embodiment, $R^{28}$ is hydroxyl.
In one embodiment, m is 1.
In one embodiment, p is 2.
In one embodiment, $R^{29}$ and $R^{210}$ are each hydrogen.
In one embodiment, $R^{29}$ and $R^{210}$ are each C(=O)OH. In one embodiment, $R^{29}$ and $R^{210}$ are joined to form a ring. In one embodiment, the ring comprises an O atom. In one embodiment, the ring comprises one or more carbonyls. In one embodiment, the ring is a 3, 4, or 5 membered ring.

In one embodiment, $R^{211}$ is a monosaccharide. In one embodiment, $R^{211}$ is glucose, fructose, or galactose.

In one embodiment, q is 2.
In one embodiment each occurrence of $Y^{21}$ is $C(R^{218}R^{219})$. In one embodiment, each occurrence of $R^{217}$ and $R^{218}$ are independently selected from hydrogen and hydroxyl.

In one embodiment, the compound is

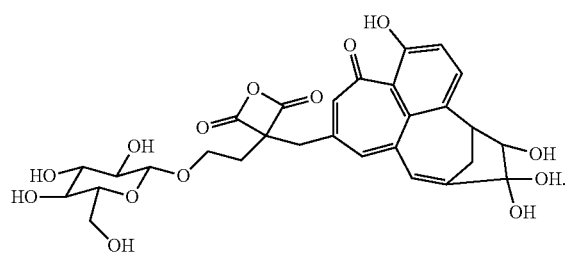 [SMILES: O=C1OC(=O)C1(CCOC1OC(CO)C(O)C(O)C1O)Cc1cc2c3c(ccc(O)c3c(=O)c1)C1CC(=C2)C(O)(O)C1O]

In one embodiment, the compound is

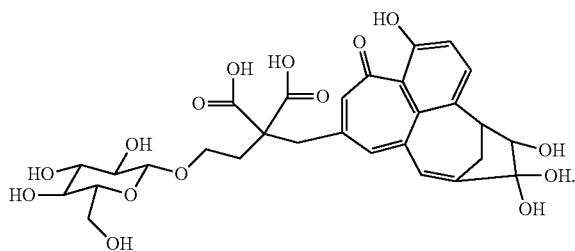 [SMILES: O=C(O)C(CCOC1OC(CO)C(O)C(O)C1O)(Cc1cc2c3c(ccc(O)c3c(=O)c1)C1CC(=C2)C(O)(O)C1O)C(=O)O]

In one embodiment, the compound is

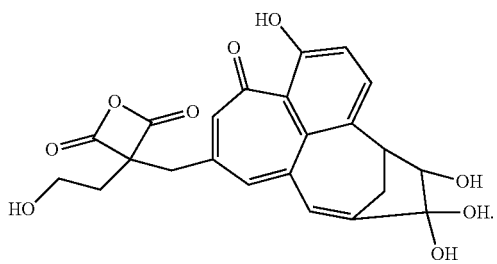 [SMILES: O=C1OC(=O)C1(CCO)Cc1cc2c3c(ccc(O)c3c(=O)c1)C1CC(=C2)C(O)(O)C1O]

In one embodiment, the compound is

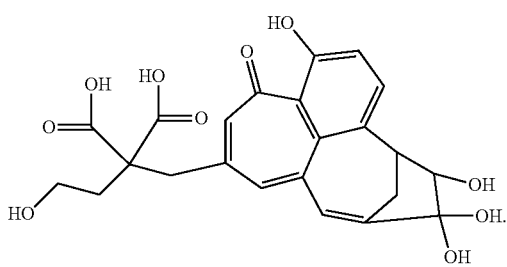 [SMILES: O=C(O)C(CCO)(Cc1cc2c3c(ccc(O)c3c(=O)c1)C1CC(=C2)C(O)(O)C1O)C(=O)O]

In one embodiment, the compound forms a dimer.

In one embodiment, the compound has a color. In one embodiment, the compound is yellow, orange, or red. In one embodiment, the compound is a blend of yellow and orange, yellow and red, or orange and red. In one embodiment, the compound is orange-red. In one embodiment, the compound is a blend of yellow, orange, or red with another color. In one embodiment, the compound is red-brown.

The compounds described herein may form salts with acids or bases, and such salts are included in the present invention. The term "salts" embraces addition salts of free acids or free bases that are compounds of the invention.

Compound Isolation

In one embodiment, compounds of the present invention may be isolated from avocado seed extract. Thus, the present invention provides a method for isolating compounds from avocado seed extract.

In one embodiment, the method comprises obtaining a seed of *Persea americana*; blending the seed; isolating supernatant from the blended seed; filtering the supernatant; lyophilizing the filtered supernatant; performing a first purification by flash chromatography to yield a first semi-pure substance; performing a second purification by reverse phase HPLC to obtain a crude substance; and performing a third purification by reverse phase HPLC to obtain to obtain a purified compound.

The step of blending avocado seeds can use any tool envisioned by a person of skill in the art. Exemplary tools include, but are not limited to, a knife, a blender, a food processor, a hammer, or a mortar and pestle. In one embodiment, the seed is mixed with a water during the blending step. In one embodiment, the water is deionized water.

In one embodiment, the method further comprises incubating the supernatant before filtering the supernatant. The step of incubating the supernatant comprises incubating the supernatant for at least one minute. In one embodiment, the incubation is for more than 30 minutes. In one embodiment, the incubation is up to 48 hours. In one embodiment, the step of incubating the supernatant comprises incubating the supernatant between 0-40° C. In one embodiment, the incubation is between 0-20° C. In one embodiment, the incubation is between 0-10° C. In one embodiment, the incubation is between 3-5° C.

In one embodiment, the supernatant is filtered.

In some embodiments, the method further comprises titrating the supernatant after filtering the supernatant. In one embodiment, the filtered supernatant is titrated to a pH of 10 using a basic solution, forming a titrated filtered supernatant. In one embodiment, the basic solution is a 1N solution of sodium hydroxide. In one embodiment, the titrated filtered supernatant is contacted with an acidic solution. In one embodiment, the acidic solution is a 1N solution of hydrochloric acid. In one embodiment, the titrated filtered supernatant is contacted with the acidic solution such that the titrated second substance has a pH less than 4. In one embodiment, the pH is less than 3.5.

In one embodiment, the supernatant is lyophilized.

The step of performing a first purification using flash chromatography comprises loading the lyophilized supernatant onto the column. In one embodiment, the lyophilized supernatant is mixed with a solvent before loading. In one embodiment, the solvent is water. In one embodiment, the solvent is deionized water. In one embodiment, the flash chromatography column comprises an Amberlite XAD7-HP resin. In one embodiment, a first semi-pure substance eluted from the column using an alcohol. In one embodiment, the alcohol is methanol, ethanol, isopropanol, butanol, or combinations thereof. In one embodiment, the first semi-pure substance is isolated in a mixture of alcohol and acetic acid.

In some embodiments, semi-pure first substance is dried before second purification step. In some embodiments, the alcohol, optionally mixed with acetic acid, is removed by evaporation. In one embodiment, the evaporation is rotary evaporation. In one embodiment, the first semi-pure substance is spray dried. In one embodiment, the first semi-pure substance is freeze dried. In one embodiment, the first semi-pure substance is lyophilized. In one embodiment, the dried first semi-pure substance is resuspended in a solvent before the isolation of the pure second substance. In one embodiment, the solvent is water. In one embodiment, the solvent is deionized water. In one embodiment, the resuspended first semi-pure substance is filtered.

In one embodiment, the second purification is a C18 reverse phase HPLC purification. In one embodiment, the performing the second purification comprises introducing the semi-pure substance to a C18 column, and eluting with a gradient of water, acetonitrile and optionally acetic acid. In one embodiment, the water is deionized water.

In one embodiment, the third purification is an Ultra Aromax® reverse phase HPLC purification. In one embodiment, the performing the third purification comprises introducing the crude substance to an Ultra Aromax® column, and eluting with a gradient of water, alcohol and optionally acetic acid. In one embodiment, the alcohol is methanol, ethanol, isopropanol, butanol, or combinations thereof.

In one embodiment, the step of obtaining an isolated final purified compound comprises isolating the product for use. In one embodiment, the final purified compound is isolated by evaporating the solvent. In one embodiment, the evaporation is rotary evaporation. In one embodiment the final purified compound is isolated by freeze drying or spray drying. In one embodiment, the final purified compound is isolated by lyophilization.

In another embodiment, the method for isolating compounds from avocado seed extract comprises obtaining a seed of *Persea americana*; grinding size reduction of the seed to obtain a slurry; incubating the slurry; extracting the compound by incubating the slurry with an alcohol to form a first mixture; isolating a first substance from the first mixture; removing the insoluble particles from the first substance; precipitating the substance to form a second mixture; isolating a second substance from the second mixture; adsorbing the second substance to a resin; and isolating the compound by eluting the compound from the resin with an alcohol (FIG. 1).

In one embodiment, the alcohol is methanol, ethanol, acetone, citric acid, acetic acid or any combination thereof. In one embodiment, the alcohol is diluted in water.

In one embodiment, the step grinding size reduction of the seed comprises two steps, a course size reduction step and a second fine reduction step.

In one embodiment, the step incubating the slurry comprises incubating the slurry for at least one minute. In one embodiment, the incubation is for more than 30 minutes. In one embodiment, the incubation is up to 48 hours. In one embodiment, the step incubating the slurry comprises incubating the slurry for at 0-40° C. In one embodiment, the incubation is at 20-40° C. In one embodiment, the incubation is at 20° C.

In one embodiment, the incubated slurry is extracted with an alcohol. In one embodiment, the alcohol is methanol, ethanol, isopropanol, butanol, or combinations thereof. In one embodiment, the alcohol is mixed with water. In one embodiment, the mixture of alcohol and water contains 5-50% water. In one embodiment, the mixture contains 20-50% water. In one embodiment, the mixture contains 30-50% water. In one embodiment, the mixture contains 35-45% water. In one embodiment, the mixture contains 40% water.

In one embodiment, the step isolating a first liquid from the first mixture comprises centrifugation or filtration through a filter.

In one embodiment, the step removing the insoluble particles from the first substance comprises filtration through a filter.

In one embodiment, precipitating the slurry comprises incubating the slurry for at least 24 hours and up to 48 hours. In one embodiment, incubating the substance comprises incubating the liquid at 4° C.

In one embodiment, the step isolating a second substance from the second mixture comprises filtration or centrifugation.

In some embodiments, the isolated second substance is titrated to a pH of 10 using a basic solution, forming a titrated second substance. In one embodiment, the basic solution is a 1N solution of sodium hydroxide. In one embodiment, the titrated second substance is contacted with an acidic solution. In one embodiment, the acidic solution is a 1N solution of hydrochloric acid. In one embodiment, the titrated second substance is contacted with the acidic solution such that the titrated second substance has a pH less than 4. In one embodiment, the pH is less than 3.5.

In one embodiment, the step adsorbing the second substance to a resin comprises applying the liquid to a XAD-7 resin. In one embodiment, the step adsorbing the second substance to a resin comprises applying the liquid to a XAD-16 resin. In one embodiment, the step adsorbing the second substance to a resin comprises applying the liquid to a PAD950 resin. In one embodiment, the step adsorbing the second substance to a resin comprises applying the liquid to a PAD900 resin.

In one embodiment, the compound is isolated by eluting the compound from the resin with an alcohol. In one embodiment, the alcohol is methanol, ethanol, isopropanol, butanol, or combinations thereof. In one embodiment, the alcohol is mixed with water. In one embodiment, the alcohol is mixed with citric acid. In one embodiment, the alcohol is mixed with both water and citric acid.

In one embodiment compound is concentrated by evaporation. In one embodiment the compound is dried by freeze drying or spray drying. In one embodiment, the dried compound is packaged for commercial distribution.

Compositions of the Invention

The invention includes a composition comprising a compound of the present invention mixed with one or more additional compounds. In one embodiment, a compound of the present invention is mixed with one or more uncolored compounds. In one embodiment, a compound of the present invention is mixed with one or more colored compounds. In one embodiment, the mixture has a different hue compared to the hue of the unmixed compounds.

The invention includes an edible composition comprising a compound of the invention. In one embodiment, the compound of the invention in the edible material is present in an amount from about 0.25 mg/mL to about 10 mg/mL. In one embodiment, the edible material comprising a compound of the invention has a hue selected from the group consisting of red, orange, and yellow.

In one aspect of the invention, compounds of the invention may be combined with one or more natural or artificial food colorants such as those approved by the U.S. Food and Drug Administration (http://www.fda.gov/ForIndustry/ColorAdditives/ColorAdditiveInventories/ucml15641.htm). In one embodiment, the natural food colorant includes, but is not limited to Citrus Red #2, safranol curcumin, capsaicin, β-carotene, bixin, and carmine, annato extract, dehydrated beets, canthaxanthin, caramel, β-apo-8'-carotenal, cochineal extract, carmine, sodium copper chlorophyllin, toasted partially defatted cooked cottonseed flour, ferrous gluconate, ferrous lactate, grape color extract, synthetic iron oxide, fruit juice, vegetable juice, carrot oil, paprika, paprika oleoresin, mica-based pearlescent pigments, riboflavin, saffron, spirulina extract, titanium dioxide, tomato lycopene extract, tomato lycopene concentrate, turmeric, and turmeric oleoresin.

In another embodiment, the artificial food colorant includes but is not limited to FD&C Blue #1, FD&C Blue #1 Aluminum Lake, FD&C Blue #2, FD&C Blue #2 Aluminum Lake on alumina, FD&C Green #3, FD&C Red #3, FD&C Red #40 and its Aluminum Lake, FD&C Yellow #5, FD&C Yellow #5 Aluminum Lake, FD&C Yellow #6, FD&C Yellow #6, FD&C Yellow #6 Aluminum Lake, titanium complexes, and Orange B.

In one aspect, the composition of the invention further comprises an aluminum-containing compound, to form an aluminum lake, wherein the unpleasantness of the taste and/or odor of the coloring material is reduced by said combination with the aluminum-containing compound. In another aspect, the composition of the invention further comprises calcium.

In another embodiment, the composition of the invention further comprises a diluent and is in a form including, but not limited to, liquids, powders, gels, and pastes.

In one aspect, the composition of the invention could be an extract of avocado seeds. In another aspect, the composition is freeze-dried or spray-dried.

Methods of the Invention

In one aspect, the present invention provides methods for coloring a material. In one embodiment, the material is an edible material, a food product, a cosmetic product, a drug product or a medical device. In certain embodiments, the material is orange. In other embodiments, the material is yellow. In yet another embodiment, the material is red. In one embodiment, the method for coloring a material comprises adding a compound of the invention to the material.

In one embodiment, the method further comprises adding a compound of the invention to the edible material at a desired concentration. In one embodiment, the concentration is from about 0.25 mg/mL to about 10 mg/mL. In one embodiment, the concentration is from about 1 ppm to 10 ppm. In one embodiment the concentration is from about 1 ppm to 100 ppm. In another embodiment the concentration is from about 1 ppm to 1000 ppm. In yet embodiment the concentration is from about 1 ppb to 10 ppb. In yet embodiment the concentration is from about 1 ppb to 100 ppb. In yet embodiment the concentration is from about 1 ppb to 500 ppb.

In some embodiments, the invention provides a method of imparting a color to a substrate. In some embodiments, the method of imparting a red, orange or yellow color to a substrate (e.g., a food item, a cosmetic, a drug or nutraceutical product, a textile product, a device such as a medical device) comprises contacting the substrate with a colorant composition comprising at least one compound of the invention described herein. In some embodiments, the colorant composition is prepared by mixing a compound herein with a color additive (e.g. a FDA approved color additive). In some embodiments, the substrate is an edible material. In some embodiments, the substrate is a food item. In some embodiments, the substrate is a medical device. In some embodiments, the substrate is a drug product. In some embodiments, the substrate is a nutraceutical product. In some embodiments, the substrate is a cosmetic product.

In certain embodiments, the amount of a colorant composition to be incorporated into a material depends on the final color to be achieved. In some embodiments, the food product, the cosmetic product, the drug product, the medical device, comprises a colorant composition disclosed herein in an effective amount, by itself or with another colorant, to impart the edible material, food product, cosmetic product, drug product or medical device a color including, but not limited to orange, yellow, and red.

In one embodiment, the invention provides a method of coloring a material, wherein the color is a yellow hue, a red hue or an orange hue.

In one embodiment, the invention provides a method of coloring a material, wherein the color is a yellow hue, including, but not limited to Amber, Apricot, Arylide yellow, Aureolin, Beige, Buff, Cadmium pigments, Chartreuse, Chrome yellow, Citrine, Citron, Color term, Cream, Dark goldenrod, Diarylide pigment, Ecru, Flax, Fulvous, Gamboge, Gold, Goldenrod, Hari, Harvest gold, Icterine, Isabelline, Jasmine, Jonquil, Khaki, Lemon, Lemon chiffon, Lime, Lion, Maize, Marigold, Mikado yellow, Mustard, Naples yellow, Navajo white, Old gold, Olive, Or (heraldry), Peach, Pigment Yellow 10, Pigment Yellow 16, Pigment Yellow 81, Pigment yellow 83, Pigment yellow 139, Saffron, Sage, School bus yellow, Selective yellow, Stil de grain yellow, Straw, Titanium yellow, Urobilin, or Vanilla.

In one embodiment, the invention provides a method of coloring a material, wherein the color is a red hue, including, but not limited to, Scarlet, Imperial red, Indian red, Spanish red, Desire, Lust, Carmine, Ruby, Crimson, Rusty red, Fire engine red, Cardinal red, Chili red, Cornell Red, Fire brick, Redwood, OU Crimson, Dark red, Maroon, Barn red, and Turkey red.

In one embodiment, the invention provides a method of coloring a material, wherein the color is an orange hue, including, but not limited to, Papaya whip, Peach, Apricot, Melon, Atomic tangerine, Tea rose, Carrot orange, Orange peel, Princeton orange, UT Orange, Spanish orange, Tangerine, Pumpkin, Giants orange, Vermilion (Cinnabar), Tomato, Bittersweet, Persimmon, Persian orange, Alloy orange, Burnt orange, Bittersweet shimmer, Brown. In one embodiment the yellow hue has a wavelength from 585 nm-620 nm.

The effectiveness of the colorant composition can be determined by comparing (e.g., by visual comparison) a color to be achieved (e.g., a red) with the product or device colored with an amount of the colorant composition.

In one aspect, the compounds of the invention can be used in cosmetic settings. In another aspect of the invention the compounds can be used for coloring drugs. In yet another application, the compounds can be used to color nutritional supplements.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Perseorangin: A Natural Pigment from Avocado (*Persea americana*) Seed The data presented herein demonstrates the colorant properties of an avocado (*Persea americana*) seed extract, and identifies the major colored compound. The extract produced a range of colors from pale yellow near pH 2.5 to deep red and brown colors near pH 10. Structural analysis of the major colored compound was performed using a variety of methods including mass spectrometry, IR and NMR spectroscopy. It is described herein that a new glycosylated benzotropone bearing compound, henceforth named perseorangin, was found to be the main molecule responsible for the color of the extract.

The materials and methods are now described.

Isolation of the Pigment

Preparation of a Semi-Pure Colored Seed Extract:

After removal from the avocados, seeds were cleaned, peeled and chopped by hand into small pieces that were then blended with 5 volumes of deionized water in a laboratory for 60 seconds. The resulting seed/water mixture was placed in the refrigerator at 4° C. for 24 h, after which, the supernatant was gravity filtered through blotting paper (grade 703). The filtered supernatant was frozen in plastic trays and lyophilized to produce a dried, crude extract (~3.8% yield). The crude extract was further purified by flash chromatography (3 cm×60 cm column) over Amberlite XAD7-HP resin. The extract (1.5 g in 150 mL deionized water) was applied to the column, washed with 4 column volumes of deionized water to remove sugars and other hydrophilic contaminants, and the colored fraction eluted with 2 column volumes of methanol containing 0.1% (v/v) acetic acid. The organic solvent was removed in a rotary evaporator under vacuum, and the water removed by lyophilization to produce a semi-pure colored extract (~30% yield).

HPLC Purification:

The semi-pure, post-Amberlite fraction was further purified using an Agilent PrepStar® high performance liquid chromatography (HPLC) system equipped with a 440-LC fraction collector. The extract was dissolved in deionized, distilled water to a final concentration of 20 mg/mL and filtered through 0.45 µm syringe filter prior to introduction into the HPLC. Samples (1 mL) were injected and separation was achieved using a Viva C18 column (250 mm×10 mm×5 µm). The mobile phase consisted of deionized water containing 0.1% of acetic acid (solvent A) and acetonitrile (solvent B) at a flow rate of 4 mL/min. The percentage of acetonitrile increased with time as follows; 0 min, 5%; 0-40 min, 5-30%; 40-45 min, 30-95%; 45-48 min, 95%; 48-49 min, 95-5%; 49-51 min 5%. Fractions were collected at 30 s intervals (2 mL each) from 19.5 min to 26 min. The peak of interest, "perseorangin," eluted at approximately 22 min. All subsequent fractions containing perseorangin were combined and dried under vacuum to produce "crude perseorangin".

Once dried, the "crude perseorangin" samples were diluted with deionized water and subjected to an additional round of preparative HPLC using an Ultra Aromax® 250 mm×10 mm×5 µm column. Samples were resolved using a gradient of deionized water containing 0.1% acetic acid (solvent A) and methanol (solvent B) at a flow rate of 4 mL/min. The percentage of methanol was increased as a function of time as follows: 0 min, 48%; 0-13.5 min, 48-65%, 13.5-14.5 min, 65%; 14.5-15 min, 65-4%; 15-17 min, 48%. Fractions were collected at 24 sec intervals (1.6 mL each from 8.9 min to 14.5 min). The peak of interest eluted as the later of two overlapping peaks at approximately 12 min to produce "perseorangin."

"Perseorangin" fractions were combined, dried, and redissolved in deionized water. As a final purification step, "perseorangin" was separated on an Ultra Aromax® column (150 mm×4.6 mm×5 µm). Deionized water containing 0.1% acetic acid (solvent A) and methanol (solvent B) gradient was employed at a flow rate of 1 mL/min. The percentage of methanol changed with time as follows: 0-30 min, 45%-65%; 30-32 min, 65-90%; 32-34 min, 90%; 34-35 min 90-45%; 35-37 min, 45%. The peak of interest eluted at 9.5-10 min. The eluent was monitored at $\lambda_{max}$=320 nm and 445 nm.

Effect of pH on the Color

Two identical samples of post-Amberlite colored extract were prepared by dissolving 0.05 g of the extract in 10 mL distilled, deionized water. The native pH of the treatment and control samples was 3.32 and 3.42, respectively. The pH of the treatment sample was adjusted to 12.32 using 10 M NaOH, and the equivalent volume of deionized water was added to the control. Samples were photographed and then immediately adjusted to pH 1.59 with 6 M HCl and re-photographed. The final pH of the control sample was 3.50 and the treatment sample was adjusted to 3.57. In all cases, an equivalent volume of water was added to the control sample in order to maintain similar concentration of extract.

Untargeted Metabolomic Analysis

Preparation of Colored and Uncolored Seed Extracts:

Five biological replicates of both colored and uncolored extracts were prepared. Each replicate contained approximate 10 g portions from two avocado seeds, totaling 20 g of seed per replicate. Colored replicates were prepared by blending ~20 g of seeds into 400 mL of deionized, distilled water. For uncolored replicates ~20 g of seeds was blended into 400 mL of deionized distilled water containing tropolone (5 mg, 0.041 mmol). Samples were then analyzed by UPLC-MS$^n$ and principal component analysis (PCA) as described below.

Mass Spectrometry:

Samples (5 µL) were separated by reverse phase HPLC using a Prominence® 20 UFLCXR system with a Waters BEH C18 column (100 mm×2.1 mm 1.7 µm particle size) maintained at 55° C. and a 20 min aqueous acetonitrile gradient, at a flow rate of 250 µL/min. Solvent A was HPLC grade water containing 0.1% formic acid and Solvent B was HPLC grade acetonitrile containing 0.1% formic acid. The initial condition was 97% A and 3% B, increasing to 45% B at 10 min, 75% B at 12 min where it was held at 75% B until 17.5 min before returning to the initial condition. Mass spectrometry experiments were performed on a 5600 (QTOF) TripleTOF with a Duospray ion source. The capillary voltage was set at 5.5 kV in positive ion mode and 4.5 kV in negative ion mode, with a declustering potential of 80 V. The mass spectrometer was operated in Information Dependent Acquisition (IDA) mode with a 100 ms survey scan from 100 to 1200 m/z and up to 20 MS/MS product ion scans (100 ms) per duty cycle using a collision energy of 50 V with a 20 V spread. Unsupervised PCA was conducted using MarkerView™ 1.2.1, which employed a covariance matrix with Pareto scaling. Known compounds were identified using the Scripps METLIN metabolomics database.

Attenuated Total Reflection (ATR) FT-Infrared Spectroscopy (IR)

Infrared spectra were collected using a Bruker Vertex V70 spectrometer using a Harrick MVP Pro Star ATR accessory with a diamond crystal. All spectra were acquired between 4000-400 cm$^{-1}$ at 6 cm$^{-1}$ resolution by averaging 100 scans using a DLaTGS detector.

One-Dimensional (1D) NMR Experiments $^1$H and $^{13}$C-NMR experiments were conducted on a Bruker Avance III spectrometer (Billerica, Mass.) equipped with a broad band observed (BBO) nitrogen-cooled 5 mm probe operating at 500.20 and 125.77 MHz for $^1$H and $^{13}$C nuclei, respectively. All experiments were performed at 25±0.01° C. and the spectra were processed by the Bruker Topspin software package v3.2.

$^1$H-NMR:

Spectra were recorded using the following acquisition parameters: 1K scans and 4 dummy scans, 64K data points (TD), 90° pulse angle, relaxation delay 3 s to ensure quantitative results and spectral width (SW) of 12 ppm.

Baseline correction was achieved by applying a polynomial fourth order function for accurate quantitation upon integration of signals of interest. The spectra were acquired without spinning the NMR tube in order to avoid spinning side bands of the first or higher order. Chemical shifts are reported in ppm and were calibrated in reference to DMSO $d_6$ ($\delta$=2.51 ppm).

$^{13}$C-NMR:

Spectra were obtained with proton decoupling, using the inverse gated decoupled (zgig) and the fully decoupled (zgdc) methods. The spectra were recorded with spectral widths of 200 ppm using 64K data points, a 90° excitation pulse (13 µs), an acquisition time of 0.8 s, and relaxation delay of 8 s. Scans (4K) were collected and spectra was zero-filled to 128K. For all FIDs, line broadening of 1 Hz was applied prior to Fourier transform. Chemical shifts are reported in ppm from DMSO $d_6$ ($\delta$=40).

Two-Dimensional (2D) NMR Experiments

Experimental details and pertinent references for most of the 2D pulse sequences used in this study can be found elsewhere (Berger et al., 2004, 200 and More NMR Experiments, A Practical Course, Weinheim: Wiley-VCH).

Gradient Selected $^1$H-$^1$H Correlation Spectroscopy (H-H-gCOSY):

Experiments were performed in the magnitude mode using 8 dummy scans, 32 scans, and 256 increments. SW of 12 ppm in both dimensions, 2K data points (TD) in F2 dimension, and a relaxation delay of 2.0 s were used. The spectra were zero-filled to a final size of 2K×2K prior to Fourier transformation.

$^1$H-$^1$H Total Correlation Homonuclear Spectroscopy ($^1$H-$^1$H-TOCSY):

Spectra were acquired in the phase sensitive mode with TPPI, using the DISPI2 pulse sequence for spin lock. 16 dummy scans, 32 scans, and 512 increments were collected, with a SW of 12 ppm in both dimensions, 2K TD in F2 dimension, spin-lock time of 80 ms, and a relaxation delay of 2.0 s. The data points in the second dimension were increased to 2K real data points by linear prediction, and the spectra were zero-filled to a final size of 2K×2K prior to Fourier transformation. A sine-bell squared window function was used in both dimensions.

Gradient Selected $^1$H-$^{13}$C Heteronuclear Multiple Bond Correlation ($^1$H-$^{13}$C HMBC):

The experiment was performed using a low-pass J-filter (3.4 ms) and delays of 65 and 36 ms to observe long-range C—H couplings with 312 increments of 2,048 data points. The relaxation delay was 2.0 s. Zero-filling to a 2K×2K matrix and π/2-shifted sine square bell multiplication was performed prior to Fourier transformation.

Gradient Selected $^1$H-$^{13}$C Multiplicity-Edited Heteronuclear Single Quantum Coherence (HSQC-DEPT or Edited-HSQC):

The combined experiment was performed with 512×512 complex points and a spectral width of 180 ppm for $^{13}$C (F1) and 12 ppm for $^1$H (F2), 128 increments, 16 dummy scans, 32 scans, for each increment according to the echo-antiecho procedure, relaxation delay of 2 s, and 1.725 ms (¼ J) for sensitivity improvement were used. Carbon decoupling during proton acquisition was achieved by applying a GARP pulse train. The data were multiplied in $^1$H with a sine weighting function and $^{13}$C time domain was doubled by forward linear prediction prior to a cosine window function.

$^1$H Diffusion Ordered Spectroscopy (DOSY):

Experiments were performed using the STE bipolar gradient pulse pair (stebpgpls) pulse sequence. 16 scans of 16 data points were collected. The maximum gradient strength produced in the z direction was 5.35 Gmm$^{-1}$. The duration of the magnetic field pulse gradients (5) was optimized for each diffusion time (A) in order to obtain a 2% residual signal with the maximum gradient strength. The values of $\delta$ and $\Delta$ were 1.800 µs and 100 ms, respectively. The pulse gradients were incremented from 2 to 95% of the maximum gradient strength in a linear ramp. The temperature was set and controlled to 298 K with an airflow of 670 L h$^{-1}$ in order to avoid any temperature fluctuations due to sample heating during the magnetic field pulse gradients.

Molecular Modeling:

Modeling was performed for the generation of a crude 3D structure using CHEM 3D 15.1 molecular mechanics, MM2 force field and energy minimization.

The results are now described.

Colorant Properties of Perseorangin

The semi-pure perseorangin in water at a final concentration of 5 mg/mL has a pH of 3.32 and a yellow color (FIG. 2A). Adjusting the pH to neutral produced a deep orange color, and increasing the pH to 10-12 created a dark red and finally brownish red color (FIG. 2B). Returning the sample to its native pH range, or even lower to pH 1.59, produced a sample in which color was still pH dependent, but the color range had been shifted to a more orange-red range (FIG. 2C).

Figure 3A:
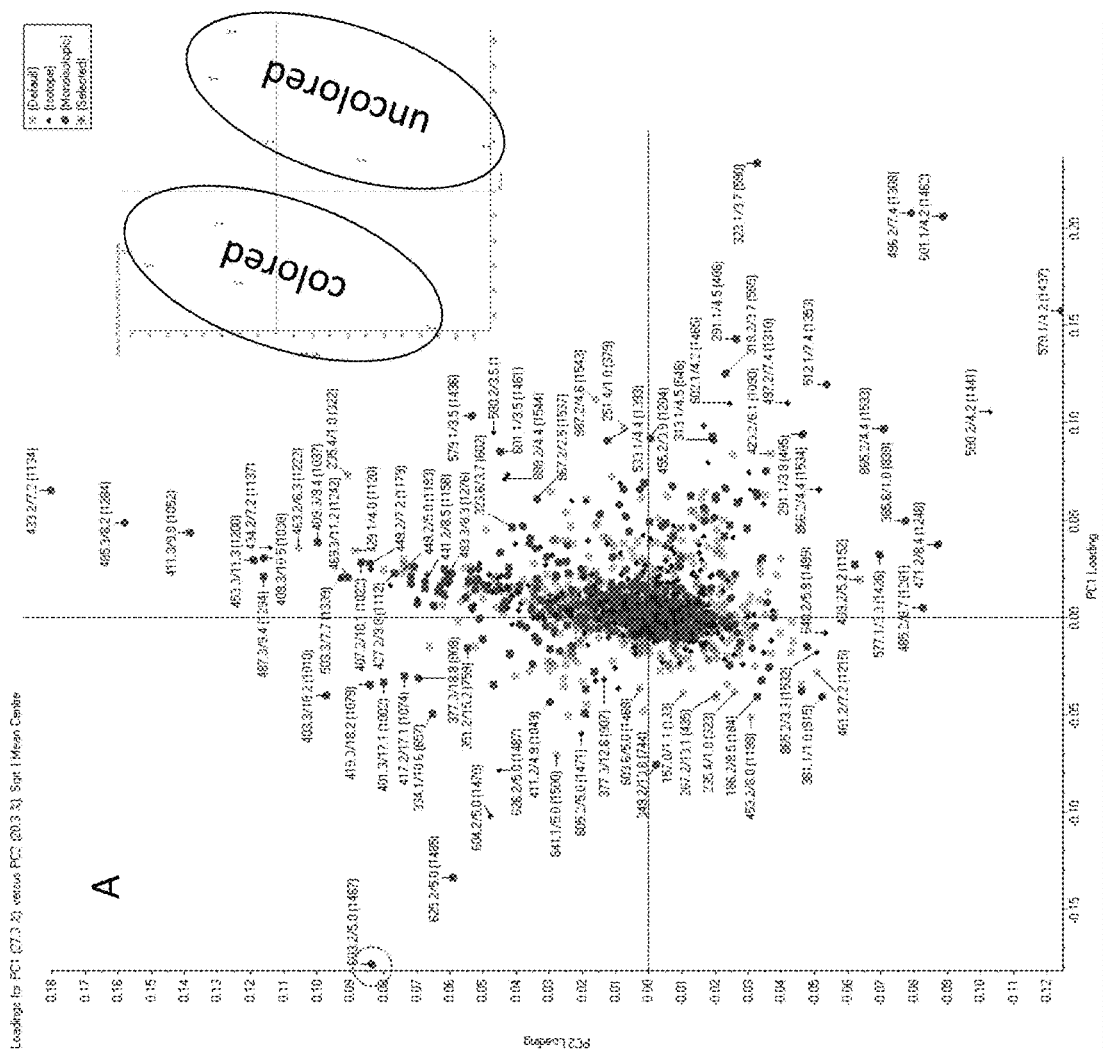
FIG. 3A and FIG. 3B, depicts principle component analysis (PCA) loadings and score plots (insets) for untargeted metabolomics analysis of colored and uncolored avocado seed extracts.
Figure 3B:
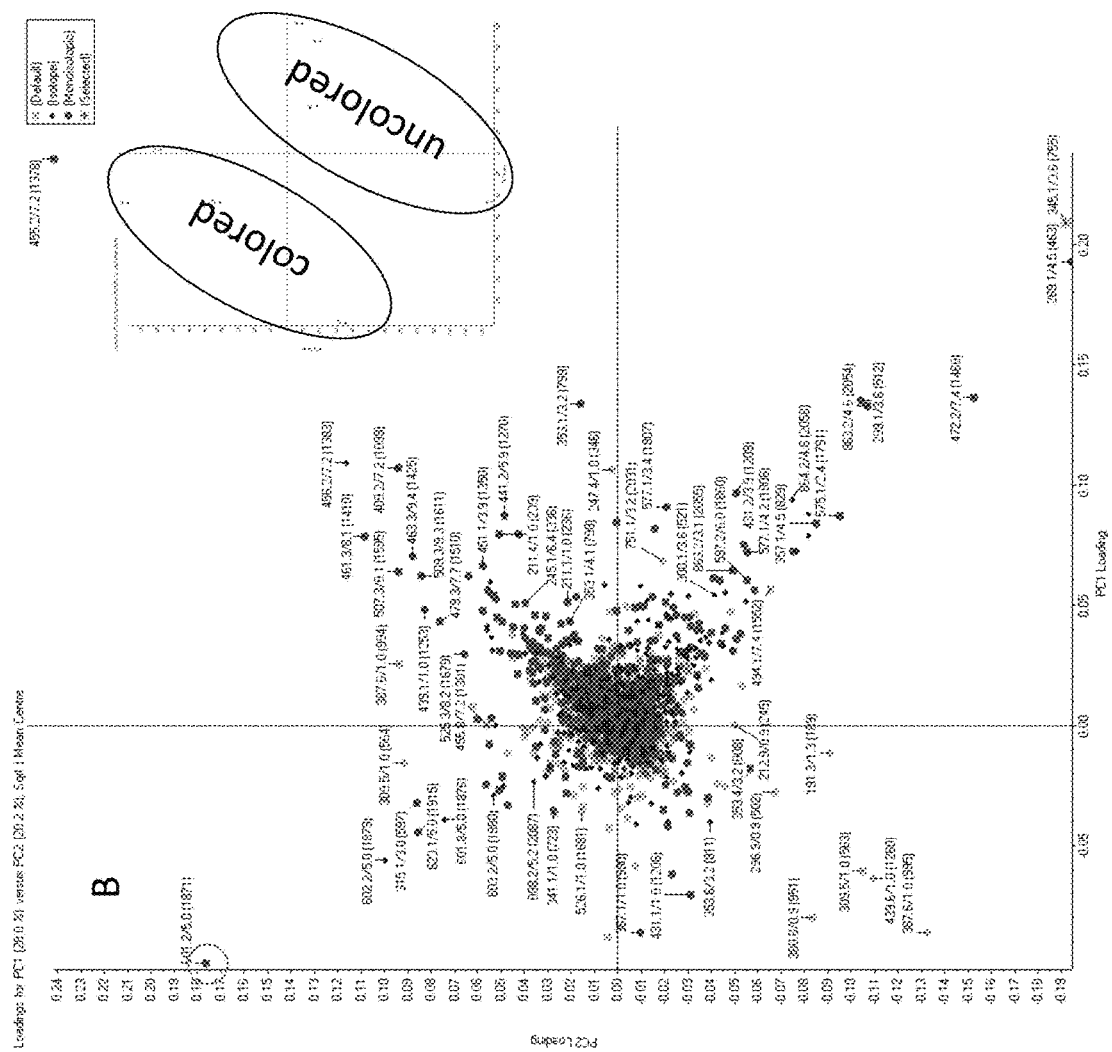

Principal Component Analysis (PCA) of Colored and Uncolored Avocado Seed Extracts To explore the phytochemical differences between colored and uncolored avocado seed extracts, a mass spectrometry-based PCA approach was used. An uncolored avocado seed extract was prepared by inhibiting the action of PPO with tropolone. By comparing biological replicates of colored and uncolored extracts, it was possible to observe compounds with masses unique to each sample. FIG. 3A shows the clustering of masses in samples analyzed in positive mode. Variation between samples is common when analyzing biological systems such as avocados and that variation can be observed by the divergence distance between clustering of replicates, as seen in the PCA scores plot in the inset of FIG. 3A. Masses near to upper left tended to be present at higher concentrations in the colored samples, while samples towards the lower right tended to be present at higher concentrations in the uncolored samples. The clustering of samples analyzed in negative mode is shown in the PCA loading plot in FIG. 3B, while the corresponding score plot for replicates is shown in the inset of FIG. 3B. Again, masses near the upper left tended to be present at higher concentrations in the colored samples, while samples towards the lower right tended to be present at higher concentrations in the uncolored samples. Approximately forty-nine compounds with mass unique to either the colored or uncolored extract were observed. Abscisic acid and perseitol, a seven carbon sugar alcohol, were present in both extracts, whereas epicatechin, catechin, proanthocyanidin B2, and salidroside were found only in the uncolored extract. Table 1 shows a list of compounds found to be unique to one or another of the extracts, of particular interest was a compound with mass 603.2 in positive mode (circled in FIG. 3A) and 601.2 in negative mode (circled in FIG. 3B) identified only in the colored extract.

TABLE 1

Compounds found in colored and uncolored avocado seed extracts via untargeted metabolomics and principal component analysis.

| Extract | Compound | Retention time (min) | Mode | Molecular Ion | Fragments |
|---|---|---|---|---|---|
| both | perseitol | 0.96 | negative | 211.082 | 193.0171, 149.0457, 131.0353, 119.0347, 113.0243, 101.025, 89.0255, 85.0309, 71.0163, 59.0173, 57.038, 55.0227 |
| both | abscisic acid | 4.05 | positive | 265.1413 | 247.1325, 135.134, 229.1225, 219.1386, 217.1219, 211.1116, 203.1054, 196.0858, 187.1131, 175.0743, 161.0945, 147.0797, 135.0791, 128.0619, 115.0552, 95.0498, 91.0547 |
| uncolored | epicatechin/catechin | 4.51 | negative | 289.073 | 271.0623, 247.0636, 245.0829, 227.0725, 221.0833, 205.0518, 203.0726, 187.0408, 161.0616, 159.0459, 151.0404, 137.0252, 125.0247, 123.0456, 109.0303, 97.0303, 95.051 |
| uncolored | catechin/epicatechin | 3.76 | negative | 289.0726 | 245.0828, 123.0459, 109.031 |
| uncolored | Procyanidin B2 | 4.17 | positive | 579.1484 | 439.1004, 427.1019, 411.1085, 409.0885, 303.0826, 301.0698, 291.0857, 289.0682, 287.0547, 259.0612, 247.0601, 229.0499, 215.0698, 205.0465, 201.0542, 191.0333, 187.0373, 179.0321, 177.0547, 175.0398, 167.0334, 165.0542, 163.0382, 159.0445, 149.0222, 147.0443, 139.0381, 135.0439, 127.039, 123.0435, 109.0304, 68.9977 |
| uncolored | salidroside | 3.67 | positive | 323.1096 | None |
| uncolored | no ID | 3.64 | negative | 299.1134 | 179.0547, 137.061, 119.0494, 101.0245, 89.025, 71.0155 |
| uncolored | no ID | 3.64 | negative | 345.1193 | 299.1134, 179.0561, 161.0457, 137.0613, 119.0439, 113.0249, 89.0255, 71.0157, 59.0168 |
| uncolored | no ID | 2.45 | negative | 575.127 | 557.1182, 531.1353, 513.41, 487.143, 449.0897, 423.0757, 407.0825, 363.0927, 351.0499, 327.0516, 325.0733, 309.0438, 307.0617, 287.0576, 243.0306, 241.0524, 217.0513, 175.041, 167.0355, 125.0245 |
| uncolored | no ID | 3.86 | negative | 431.1571 | 299.1094, 191.0582, 149.047, 119.05, 99.0113, 89.0259, 71.0144, 59.0145 |
| uncolored | no ID | 4.52 | negative | 357.0588 | 311.0537, 289.0721, 245.0821, 203.0711, 137.0245, 109.0302 |
| uncolored | no ID | 5.8 | negative | 437.0509 | 419.0418, 391.049, 285.3968, 285.0378, 284.0348, 283.0264, 227.0345, 171.0448, 151.0035, 123.0059 |
| uncolored | no ID | 4.16 | negative | 577.1356 | 451.1055, 425.0901, 407.0788, 339.0898, 289.0725, 287.0565, 245.0819, 203.0691, 137.0238, 125.0244 |
| uncolored | no ID | 3.43 | negative | 577.1423 | 559.1265, 457.1053, 425.0921, 407.0798, 339.0899, 289.0736, 245.0829, 161.0252, 125.0248 |
| uncolored | no ID | 2.42 | negative | 863.1943 | 711.1417, 693.1323, 649.1332, 575.1234, 513.123, 449.0925, 407.0818, 297.0422, 287.0565, 243.0302, 167.0353 |
| uncolored | no ID | 6.04 | negative | 597.1882 | 477.1443, 357.1041, 345.1067, 339.0859, 315.0899, 233.0458, 209.0467, 191.0366, 167.0354, 125.0244 |
| uncolored | no ID | 7.37 | negative | 540.149 | 494.1429, 472.1618, 472.1854, 350.0873, 321.0949, 254.043, 232.0646, 212.0338, 172.0403, 144.0457, 132.0454 |
| uncolored | no ID | 5.8 | negative | 575.1223 | 539.101, 449.0882, 423.0769, 407.0779, 327.0521, 289.0725, 287.0548, 285.0419, 177.0193, 175.0397, 163.0038, 125.0247 |
| uncolored | no ID | 4.17 | positive | 601.1302 | 449.0829, 431.716, 311.0526 |
| uncolored | no ID | 7.4 | positive | 496.157 | none |
| uncolored | no ID | 4.53 | positive | 291.0866 | 207.0651, 165.0548, 161.0593 |

TABLE 1-continued

Compounds found in colored and uncolored avocado seed extracts via untargeted metabolomics and principal component analysis.

| Extract | Compound | Retention time (min) | Mode | Molecular Ion | Fragments |
|---|---|---|---|---|---|
| uncolored | no ID | 3.67 | positive | 318.1545 | 265.1079, 247.0967, 229.0857, 147.0437, 139.0387, 123.0439, 115.0543, 111.0441, 91.0552, 77.0399, 65.0406, 55.0207 |
| uncolored | no ID | 7.4 | positive | 512.1319 | none |
| uncolored | no ID | 4.42 | positive | 865.1955 | 713.1505, 695.1389, 575.1172, 205.0844, 187.0751, 163.0598, 145.0497, 127.0387, 121.0653, 85.0299, 77.0401, 69.0351, 57.036, 53.0416 |
| uncolored | no ID | 3.8 | positive | 291.0859 | 207.0643, 179.0682, 165.0539 |
| uncolored | no ID | 3.67 | positive | 470.1613 | 399.0965, 339.0746, 320.1014, 161.0598, 147.0436, 139.0388, 123.0439, 119.0485, 115.0544, 111.0438, 91.0554, 77.0391 |
| uncolored | no ID | 4.53 | positive | 313.0674 | 279.0533 |
| uncolored | no ID | 4.64 | positive | 575.1019 | 539.098, 529.134, 279.0533, 261.0269, 251.0664, 219.0314, 201.0065, 177.0222, 170.406, 158.9965, 140.9861, 121.0652, 98.9752, 77.0406 |
| uncolored | no ID | 1.04 | positive | 365.6434 | 203.052, 185.0414 |
| uncolored | no ID | 8.35 | positive | 471.2209 | 335.095 |
| uncolored | no ID | 3.33 | positive | 577.1332 | 541.1306, 451.0998, 449.0806 |
| uncolored | no ID | 3.66 | positive | 385.081 | 339.3446 |
| uncolored | no ID | 4.56 | positive | 330.0386 | 311.4504, 279.0465, 237.0408, 201.0073, 175.005, 163.006, 126.969, 110.9749, 98.9766, 68.9664 |
| uncolored | no ID | 4.03 | positive | 617.6813 | 311.0522, 287.0526, 191.0045, 173.019, 160.9945, 140.0411, 139.0389 |
| uncolored | no ID | 4.53 | positive | 329.041 | 190.9962, 172.9939, 160.988 |
| uncolored | no ID | 7.4 | positive | 336.107 | 192.0642, 174.0522, 146.0596, 132.9961 |
| uncolored | no ID | 5.27 | positive | 383.1665 | 221.1129, 128.049 |
| uncolored | no ID | 3.9 | positive | 471.1259 | None |
| uncolored | no ID | 4.8 | positive | 577.1338 | 559.1175, 451.0739, 435.0754, 409.0917, 301.0684, 289.0726, 275.0703, 271.0583, 245.0411, 163.0373, 123.0434 |
| colored | no ID | 4.99 | negative | 603.1596 | 449.1087, 439.1136, 421.0948, 299.0563, 271.0261, 259.0621, 175.04 |
| colored | no ID | 4.99 | negative | 623.1428 | 471.0916, 449.1119, 381.0565, 293.0443, 269.0619, 269.0464, 227.0335 |
| colored | no ID | 3.34 | negative | 447.1531 | 315.108, 191.0565, 174.9567, 135.0455, 89.0257 |
| colored | no ID | 4.96 | negative | 733.2036 | 581.1564, 571.1712, 439.1058, 421.0892, 259.0599 |
| colored | no ID | 5.18 | negative | 887.2102 | 725.1714, 449.1034, 394.0628 |
| colored | no ID | 4.99 | negative | 691.1336 | 645.1358, 623.1358, 623.1447, 539.0832, 471.0935, 449.1107, 381.0565, 309.0367, 293.4312, 269.0458, 225.0515 |
| colored | no ID | 4.99 | negative | 601.4094 | none |
| colored | no ID | 10.59 | positive | 334.1114 | 306.1059, 230.0734, 229.0682 |
| colored | no ID | 5.01 | positive | 625.6052 | 473.1048, 311.0514, 203.0624, 127.0308, 126.0243, 105.0458, 77.0403, 58.9978, 51.0265 |
| *colored | no ID | 5.01 | positive | 603.169 | 451.1201, 441.1167, 395.1102, 289.0697, 271.0589, 243.0636, 215.0697, 147.0432 |

*[M + H]+ 603.169 was explored further in these studies

Compound Identification

Figure 4:
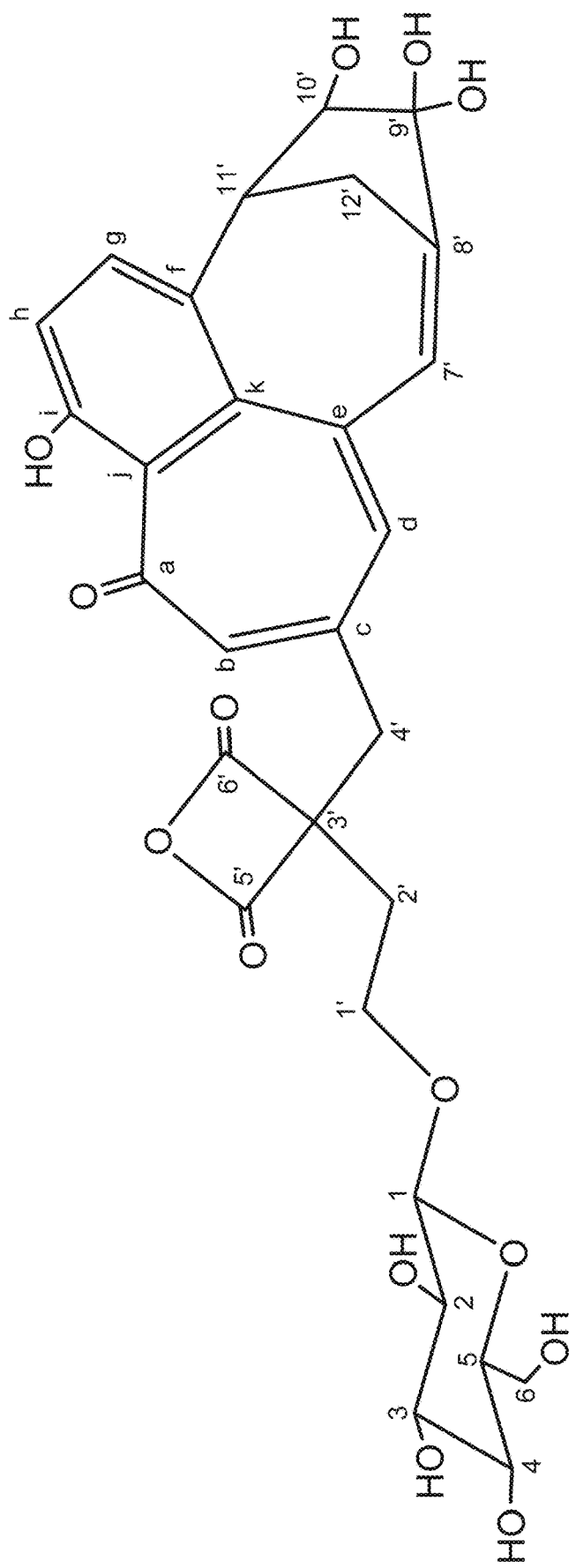
FIG. 4 depicts the proposed chemical formula and the numbering system of perseorangin.

The proposed chemical formula of perseorangin, as identified by NMR and MS, and the numbering system of the investigated molecule are presented in FIG. 4. The purified compound collected from the Ultra Aromax® column appeared as a yellow-orange solid and was analyzed via high-resolution mass spectrometry. The molecular formula of the compound was determined to be $C_{29}H_{30}O_{14}$ with a mass of ca. 602.16. It shows a main ion with m/z 603.1675 [M+1] in the positive mode and corresponds to a degree of unsaturation equal to 15. An [M+1] ion with m/z 1205 produced by the combination of two 603 units indicates the existence of a dimer. The formation of a dimer is thought to be favored because of the high-energy strain of some cyclic units in the molecules, as well as the stacking between the rings of benzotropone due to π-π interactions. The MS/MS analysis also showed the presence of an abundant m/z 441.1160 fragment (Δm/z 162) indicating the presence of a hexose moiety.

IR Spectroscopy

Figure 5:
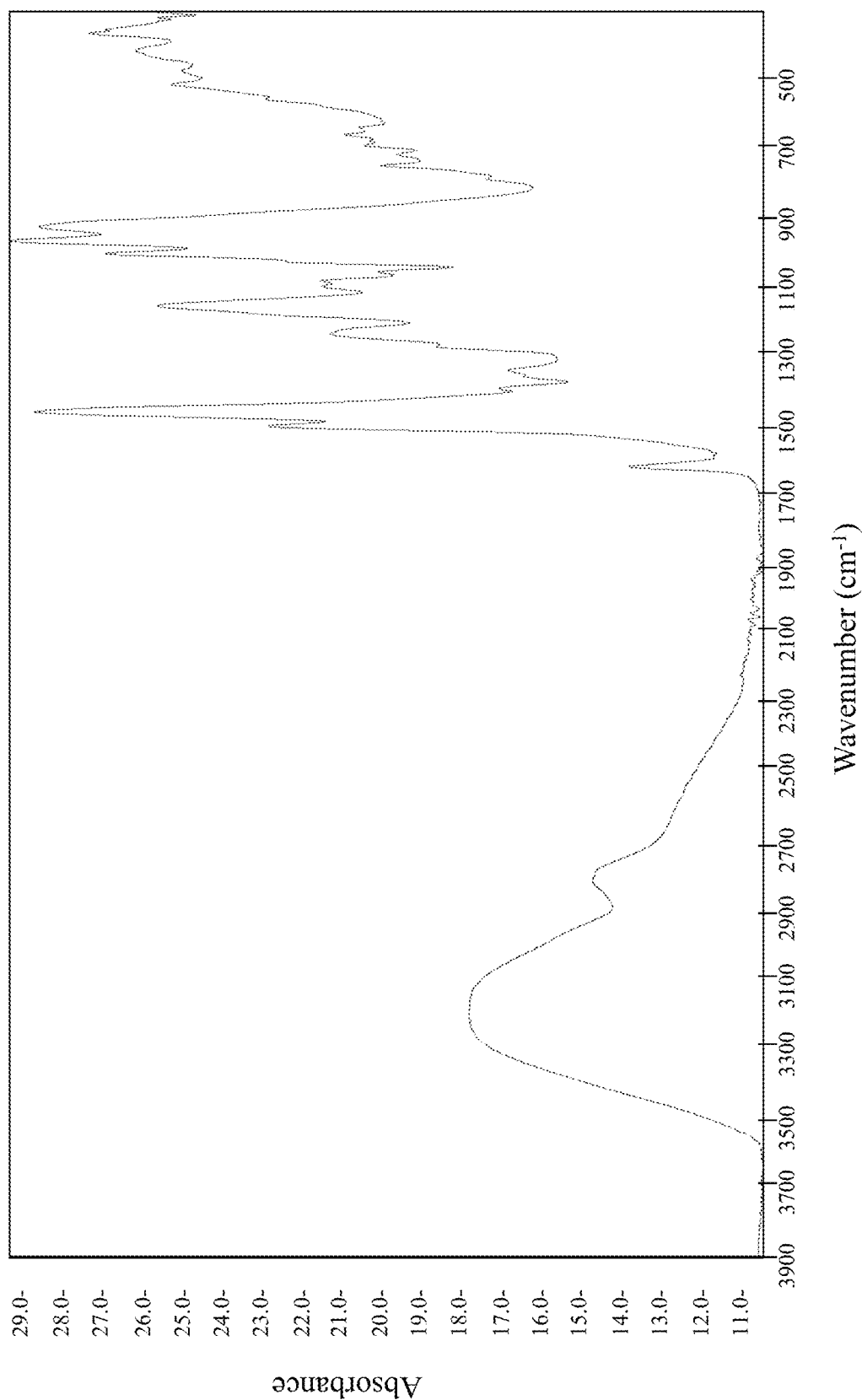
FIG. 5 depicts the ATR-FTIR spectrum of neat perseorangin.
Figure 6:
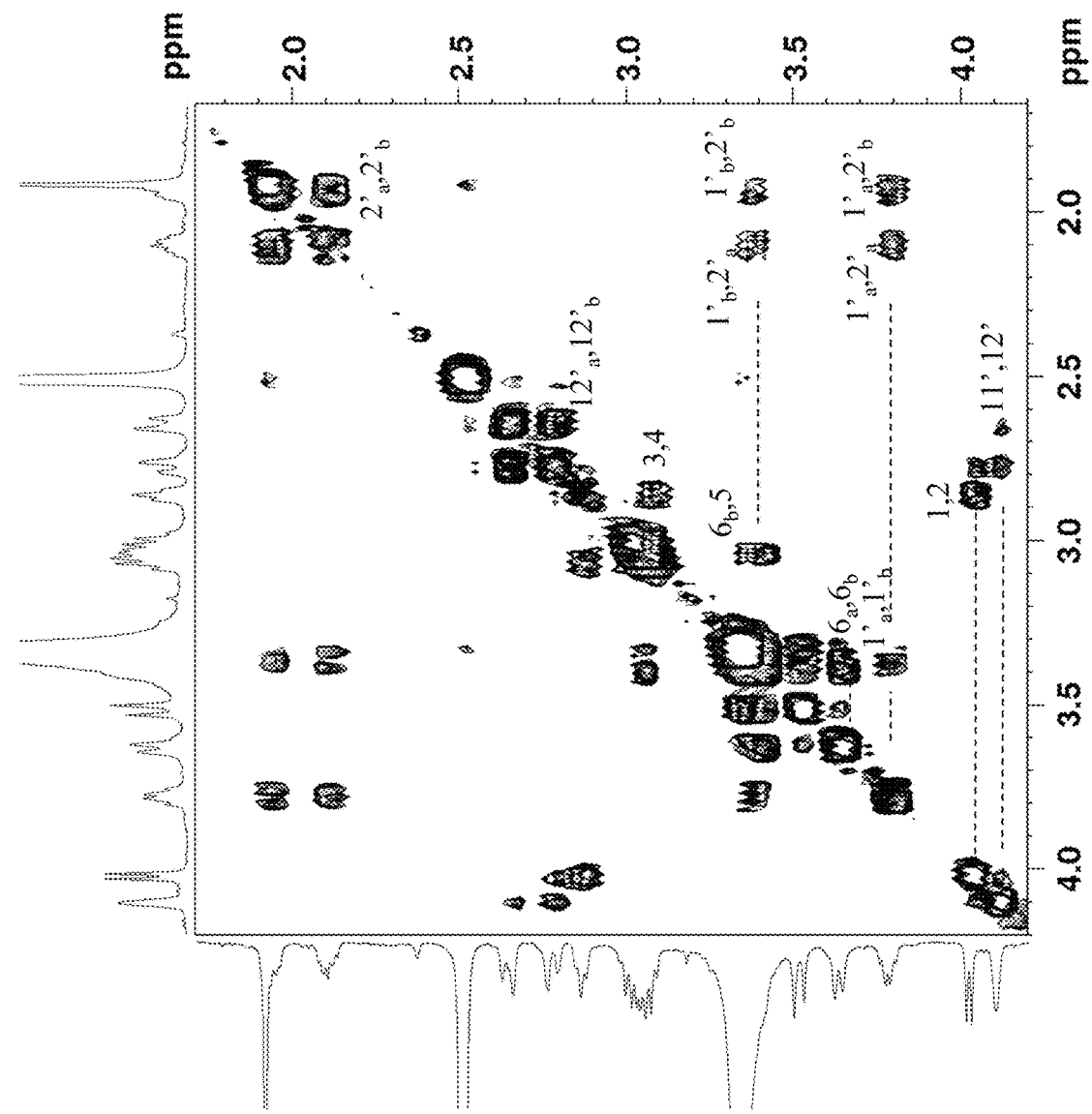
FIG. 6 depicts the $^1$H-$^1$H-gCOSY spectrum of perseorangin.

ATR-FTIR analysis revealed a broad OH band at 3300 cm$^{-1}$ and a peak at 1640 cm$^{-1}$ indicating the presence of C=O stretches. Although imines also absorb in that wavenumber, the stoichiometric analysis showed that no nitrogen appears in the compound. In addition, benzotropones have been previously reported to absorb in similar wavenumbers (Remias et al., 2012, FEMS Microbiology Ecology, 79:638-648). The IR spectrum of perseorangin is shown in FIG. 5. $^1$H and $^{13}$C NMR Assignment The correct $^1$H and $^{13}$C NMR assignments for the purified compound are based on the 1D and 2D NMR experiments and take into consideration factors such as chemical shifts, multiplicities due to scalar couplings and the relative integration values of various NMR signals. Although perseorangin is soluble in water, DMSO d$_6$ was the preferred solvent because NMR spectra with higher quality and resolution were produced. The colorant compound is a glycoside and the starting point for the NMR assignment was the anomeric proton H1 of the sugar moiety, which gives a characteristic doublet at δ 4.02 with a $^2J_{(1,2)}$ of 7.7 Hz due to coupling with proton H2 at δ 2.86 (Table 2). This coupling constant value is characteristic of the β-D-glucopyranose ring (Remias et al., 2012, FEMS Microbiology and Ecology, 79:638-648) in which the angle at H1-C1-C2-H2 is about 180°. The β-glucopyranose ring conformation has reduced steric hindrance because all hydroxyl groups are equatorial and thus it is energetically favored. The COSY (FIG. 6) and TOCSY spectra (FIG. 7) allow the identification of the sugar protons H3 at δ 3.07, H4 at δ 3.00, H5 at δ 3.03, as well as the methylene protons H6a and H6b at δ 3.63 and δ 3.40 respectively, which all belong to the same spin system, as shown in FIG. 3 and have cross peaks with each other. The chemical shifts of carbons C1, C2, C3, C4, C5 and C6 at δ 103.33, δ 73.84, δ 76.89, δ 70.34, δ 77.24 and δ 61.45, respectively, of glucopuranose can be easily assigned from the correlation peaks they have with the corresponding protons in the HSQC-DEPT spectrum (FIG. 8), which combines the usual one C—H bond correlation (gHSQC) together with carbon multiplicity selection similar to that obtained by the DEPT-135 experiment.

Figure 8:
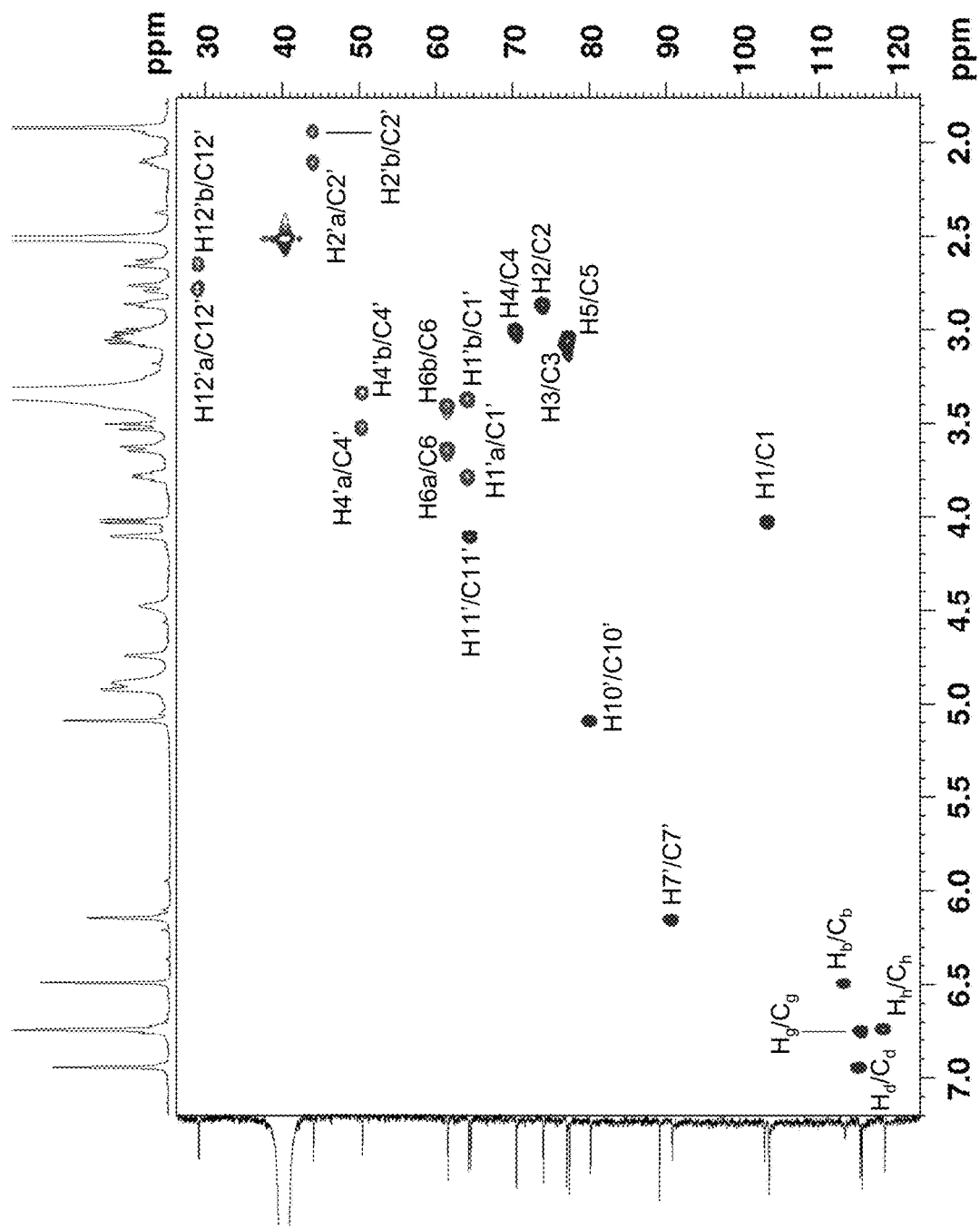
FIG. 8 depicts the HSQC-DEPT (500 MHz) spectrum of perseorangin in DMSO-$d_6$ solution. Spectra show one-bond correlations between protons and carbons; negative signals (red) for the $CH_2$ carbons and positive signals (blue) for the CH carbons.
Figure 9:
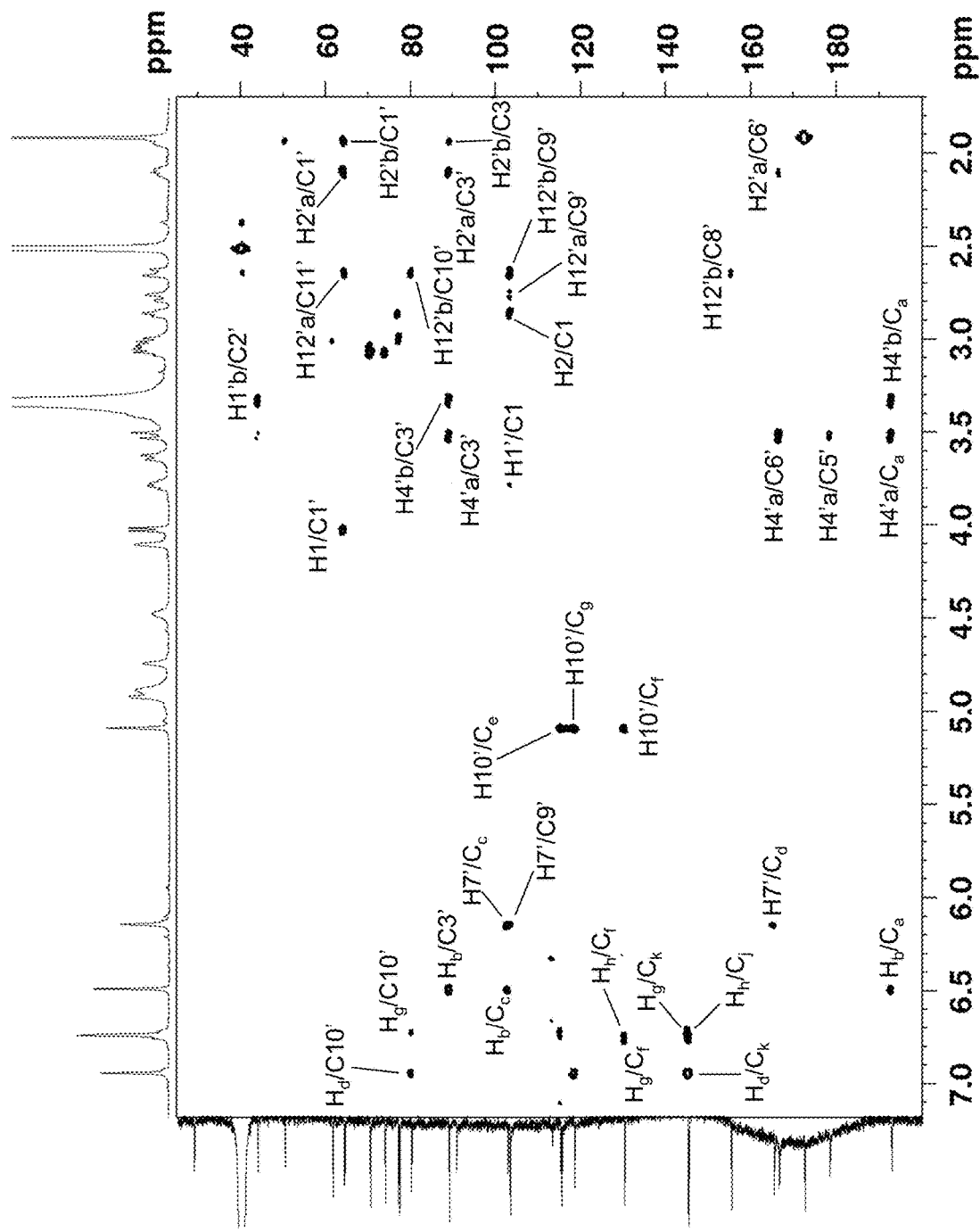
FIG. 9 depicts the 500 MHz $^1$H-$^{13}$C gHMBC spectrum of perseorangin acquired over a 200 ppm spectral width in DMSO $d_6$ solution.

The sugar ring is bound to the aglycone through its anomeric carbon via an O-glycosidic bond between the oxygen atom of the anomeric carbon and the methylene carbon C1' at δ 64.12 of the butyl group, as indicated by the correlation peaks between H1 and C1', in the HMBC spectrum, shown in FIG. 9. The corresponding diastereotopic protons H1$_a$' and H1$_b$' appear at δ 3.78 and δ 3.37 respectively as shown in the HSCQ-DEPT spectrum (FIG. 8). The H1$_a$' and H1$_b$' protons form a short spin system with the H2$_a$' and H2$_b$' methylene protons at δ 2.10 and δ 1.93, as found by their cross peaks in the COSY spectrum and the correlation peaks between C2' at δ 43.86 and H1$_a$'/H1$_b$' in the HMBC spectrum. The H2$_a$' and H2$_b$' protons have an HMBC peak with the quaternary carbon C3' at δ 89.00. C$_3$' has HMBC correlations with the methylene H4$_a$'/H4$_b$' at δ 3.52 and at δ 3.33, as well as an unusual four-bond correlation with the benzotropone proton H$_b$ at δ 6.49. The H2' and H4' protons have correlation peaks in the HMBC spectrum with the carboxylic carbon C6' at δ 166.61, whereas only H4' protons have an HMBC signal with carboxylic carbon C5' at δ 178.39. Protons H4$_a$'/H4$_b$' have also HMBC signals with the carbonyl carbon C$_a$ at δ 192.80, which is a typical chemical shift value for a benzotropone carbonyl carbon (Lewis et al., 1998, Phytochemistry, 49:2511-2519; Sang et al., 2004, Bioorganic & Medicinal Chemistry, 12:459-467), further confirming the attachment of the aliphatic butyl chain on the benzotropone ring.

Carbon C$_a$ has an HMBC signal with proton H$_b$ which appears as a singlet in the 1D $^1$H NMR spectrum indicating the absence of a neighboring proton, observation that is further confirmed by the lack of cross peaks in the COSY and TOCSY spectra. Proton H$_d$ at δ 6.95, also appears as a singlet, however it displays a cross peak in the TOCSY spectrum with the aromatic signal at δ 6.74 which belongs to protons H$_h$ and H$_g$ at δ 6.72 and δ 6.75 respectively. The integral of the signal at δ 6.74 accounts for two protons and a closer inspection reveals the presence of two non-symmetrical doublets characterized by a strong roof effect, where the outer lines become weaker and the inner signals become more intense. This is because of the close isochronicity and the strong scalar coupling (Δδ/J<10) of the H$_h$ and H$_g$ protons that form a strongly coupled AB spin system, generating spectra with second order effects. The corresponding methine carbons of benzotropone C$_h$, C$_g$, C$_d$ and C$_b$ appear at δ 118.35, δ 115.41, δ 115.16 and δ 113.17 as found by the HSQC-DEPT experiment. C$_b$ has a broad signal of low intensity probably due to a short T$_2$ relaxation time, and the short T$_2$ may be the reason that we were not able to identify quaternary carbon C$_i$. Quaternary carbons C$_c$, C$_j$, C$_k$ and C$_f$ appear at δ 102.77, δ 145.40, δ 145.30 and δ 130.12 as found from the HMBC spectrum.

Figure 10:
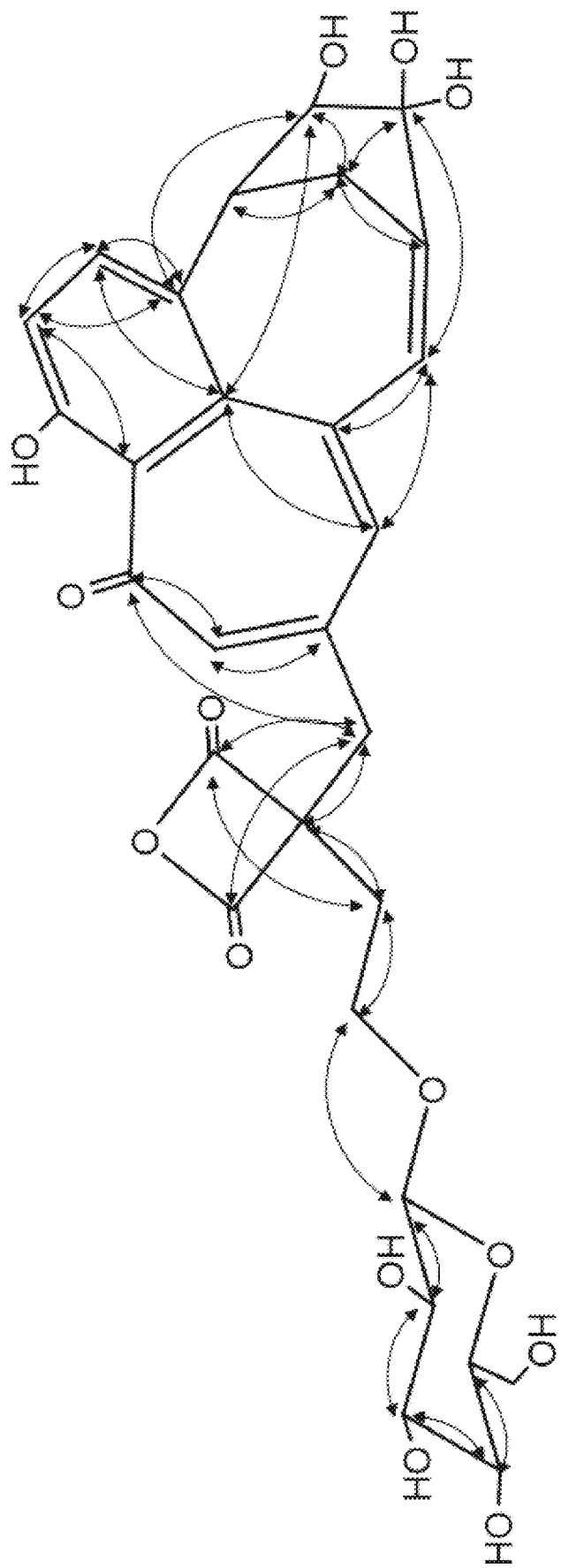
FIG. 10 depicts the diagnostic HMBC correlations in perseorangin using bidirectional arrows.
Figure 11:
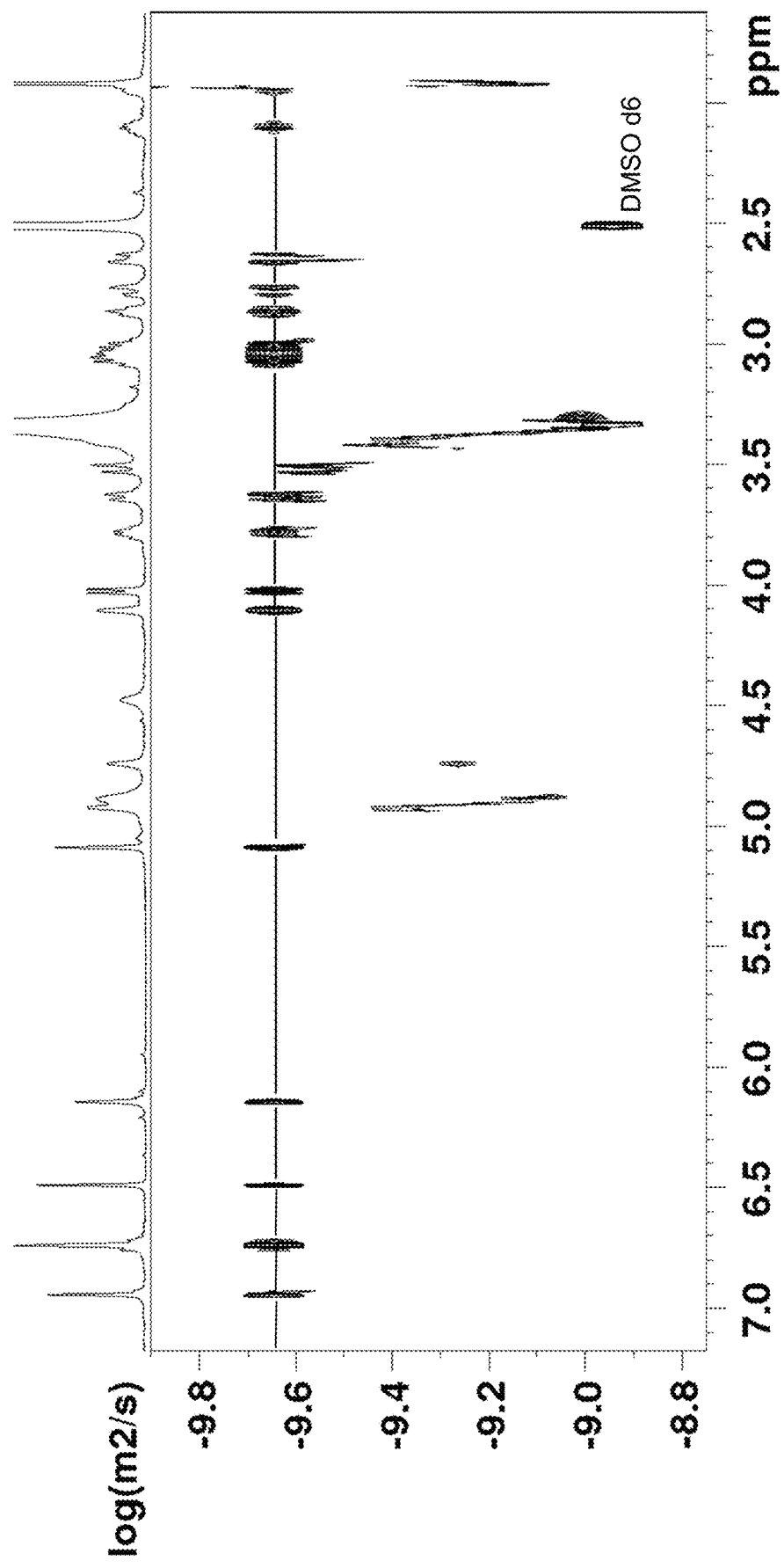
FIG. 11 depicts the $^1$H DOSY (500 MHz) plot of perseorangin in DMSO-$d_6$.
Figure 12:
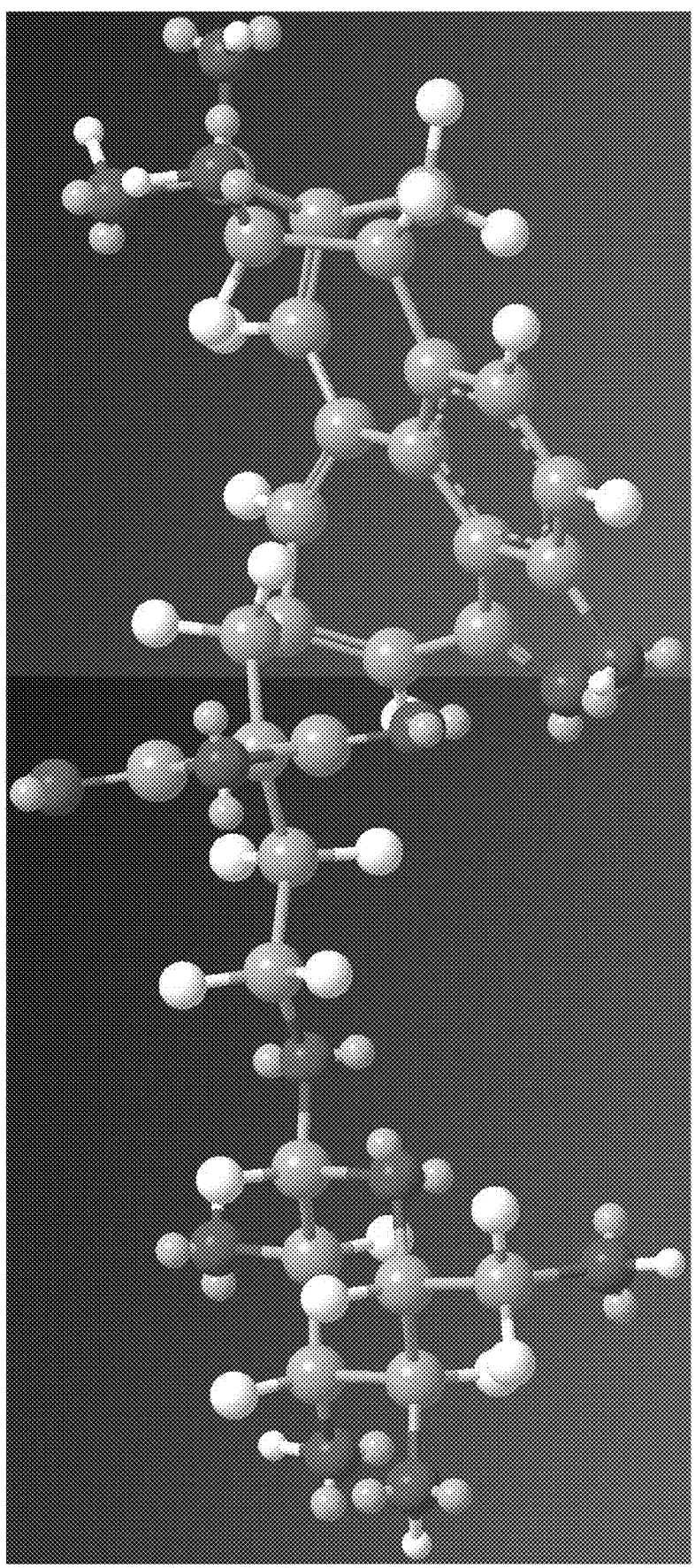
FIG. 12 depicts a 3D representation of the lowest energy conformer of perseorangin calculated by molecular mechanics.

Carbons C$_g$ and C$_f$ have cross peaks in the HMBC spectrum with methine proton H10' at δ 5.08, indicating the attachment of a side chain in a para position relative to the —OH group of carbon C$_i$ of the benzotropone ring. The C$_i$ carbon could not be identified, however it appears to overlap with C6', because its signal is associated with an integral that corresponds to more than one carbon, as found by the semi-quantitative inverse gated decoupling $^{13}$C experiment. H10' forms a spin system with proton H11' at δ 4.10, and protons H12$_a$'/H12$_b$' at δ 2.77/2.64 as indicated by their cross peaks in the TOCSY spectrum. Because the NMR experiments were run in DMSO d$_6$, cross peaks between exchangeable protons, such as the OH proton of carbon C10' at δ 4.92 and aliphatic protons such as H10' and H12$_a$'/H12$_b$' are also visible in the TOCSY spectrum. The chemical shifts of the corresponding carbons C10', C11' and C12' at δ 64.39, δ 80.00 and δ 28.94 respectively can be easily assigned by the HSQC-DEPT spectrum. Further confirmation for the para regiochemistry arises from the correlation peaks in the HMBC spectrum of protons H$_g$ and He of benzotropone with carbon C11'. Protons H12' have HMBC signal with the quaternary carbon C9' at δ 103.30, which bears two hydroxyl groups and thus appears downfield. In addition, H12$_b$' has a correlation peak in the HMBC spectrum with the quaternary olefinic carbon C8' at δ 155.40. The olefinic proton H7' appears at δ 6.14 and is directly attached to carbon C7' at δ 90.85 as found in the HSQC-DEPT spectrum. The chemical shift of C7' is relatively unusual for an olefinic carbon, in terms that appears up-field, however similar shielding effects have been previously reported for benzotropones (Klostermeyer et al., 2000, European Journal of Organic Chemistry, 13:603-609). H7' has also an HMBC correlations with C9', C$_c$ and C$_d$. The $^1$H and $^{13}$C chemical shifts of the compound are given in Table 2. FIG. 10 shows the key diagnostic correlations in perseorangin, which indicate the connectivity between various units. Further evidence arises from the DOSY spectrum (FIG. 11) that confirms the presence of one molecule as all peaks are aligned on the same diffusion coefficient value. FIG. 12 shows the 3D representation of the molecule as determined by molecular mechanics (MM2) force field calculations having as starting point a crude model structure and gradually converted to a 3D conformation by energy minimization.

Perseorangin proved to be a stable molecule even over a variety of light and temperature conditions (Shegog, 2015, Characterization of Perseorangin a Natural Orange Pigment found in Hass Avocado (*Persea americana*) Seed and its Uses as a Natural Food Colorant, PhD Thesis, The Pennsylvania State University). This is probably due to its aromaticity as the benzotropone unit can be considered as a ten-electron aromatic system. The septa-triene-none moiety of benzotropone is already close to an aromatic system (6 pi-electrons) due to the partial positive charge on $C_a$. The triene can close its cyclic conjugation by interacting the triene pi-electron density with the in-phase and empty C═O pi-antibonding orbital. The hydrogen-bonding interaction with the —OH group would further decrease the energy level of C═O pi-antibonding orbital, making the antibonding orbital even more energetically accessible to the triene and thus enhance the aromaticity even further. Despite the high energy strain of the five-member ring at the position of carbon C8', which disrupts the planarity of the seven-member ring, as shown by MM2 calculations, the compound seems to be aromatic, as indicated by its stability and the chemical shifts of protons $H_b$ and $H_d$. The formation of the dimer, which is consistently detected in MS, may occur through the breaking of the strained double bond of C8' of the five-member ring or of the cyclopropyl ether ring. The detection of a compound with m/z 603.1687 may correspond to an ion radical of perseorangin may indicate the formation of the dimer through a radical mechanism. The extensive conjugation of perseorangin, which can stabilize such a radical ion, may support this assumption, however, further experiments are required to confirm this hypothesis.

Perseorangin appears as an orange-yellow solid. It is characterized by extensive conjugation since 14 π electrons from C═C and C═O bonds are involved in the conjugation. In addition, the lone pair of electrons from the hydroxyl group on $C_i$ could also participate in the conjugation and form a 16 π electron system. This extensive conjugation is responsible for a low HOMO-LUMO gap, causing a bathochromic shift that explains the orange-yellow color of the compound.

TABLE 2

| Position | $^1$H δ | $^{13}$C δ |
|---|---|---|
| 1 | 4.02, d (7.7 Hz) | 103.33 |
| 2 | 2.86, dd (9.9/7.7 Hz) | 73.84 |
| 3 | 3.07, bt (9 Hz) | 76.89 |
| 4 | 3.00, bt (9 Hz) | 70.34 |
| 5 | 3.03, ddd (13, 9, ~1 Hz) | 77.24 |
| $6_a$ | 3.63, d (11.59 Hz) | 61.45 |
| $6_b$ | 3.40, d (11.59 Hz) | |
| $1'_a$ | 3.78, ddd (15, 9, 2 Hz) | 64.12 |
| $1'_b$ | 3.37 (Obscured by the water signal) | |
| $2'_a$ | 2.10, ddd (14.6, 9, ~1 Hz) | 43.86 |
| $2'_b$ | 1.93 ddd (14.6, 9, 6 Hz) | |
| 3' | N/A | 89.00 |
| $4'_a$ | 3.52 d (14.71 Hz) | 50.24 |
| $4'_b$ | 3.33 (Obscured by the water signal) | |
| 5' | N/A | 178.39$^a$ |
| 6' | N/A | 166.61$^a$ |
| a | N/A | 192.80 |
| b | 6.49 s | 113.17 |
| c | N/A | 102.80 |
| d | 6.95 s | 115.16 |
| e | N/A | 165.32 |
| f | N/A | 130.12 |
| g | 6.76 d (8.4) | 115.41 |
| h | 6.72 d (8.4) | 118.35 |
| i | N/A | Not identified |
| j | N/A | 145.40 |
| k | N/A | 145.30 |
| 7' | 6.14 s | 90.85 |
| 8' | N/A | 155.40 |
| 9' | N/A | 103.30 |
| 10' | 5.08 | 80.00 |
| 11' | 4.10 | 64.39 |
| $12'_a$ | 2.77 dd (16.4, 3.9) | 28.94 |
| $12'_b$ | 2.64 dd (16.4, ~1) | |

$^a$indicates that the assignments may be interchanged.

Therefore, the experiment evidence suggests that, although the mixture contains a number of colored compounds that contributed to the final color of the extract, perseorangin, a benzotropone-bearing compound with an unusual chemical structure, different from any other reported natural or synthetic pigment, seems to play a central role on the final color.

Example 2: Use of Pigment in Personal Care Products, Home Care Products, and Edible Materials Example 2A—0.01% of avocado seed extract prepared according to the flow diagram attached was added to an uncolored commercial bubble bath (Sesame Street Extra Sensitive Bubble Bath manufactured by The Village Company) to produce an orange product.

Example 2B—0.02% of avocado seed extract prepared according to the flow diagram attached was added to an uncolored commercial window cleaner to produce a yellow product.

Example 2C—from 0.02-0.08% of avocado seed extract prepared by the attached flow diagram was added to a commercial sugar-free vanilla-flavored pudding to produce an orange-red colored product of varying color intensity.

Example 3: Perseorangin: A Natural Pigment from Avocado (*Persea americana*) Seed In this study, the isolation and characterization of the most abundant pigment in colored avocado seed extract (CASE) is described. The pigment, perseorangin, was studied using liquid chromatography-mass spectrometry (LC-MS), and infrared (IR) and nuclear magnetic resonance spectroscopy (NMR). Given the observed similarities to theaflavins (e.g. PPO mediated origin, color, and the presence of similar biosynthetic precursors in the seed), it was hypothesized that this compound contains a benzotropolone or benzotropone moiety.

The materials and methods are now described.

Materials

Avocados (Hass variety) were sourced from local grocery stores. HPLC-grade methanol and acetonitrile were purchased from VWR (Radnor, Pa., USA). Amberlite XAD7-HP and $d_6$-dimethylsulfoxide were purchased from Sigma Chemical Co. (St. Louis, Mo., USA). All other reagents were of the highest grade commercially available. Organic solvents were removed using a rotary evaporator (Heidolph, Germany). Water was removed using a Virtis Genesis 25 XL Pilot Lyophilizer (Warminster, Pa., USA).

Isolation of the Pigment

After removal from the avocados, seeds were cleaned, peeled and chopped by hand into small pieces and then blended with 5 volumes of deionized water in a laboratory blender (Waring, Wilmington, N.C., USA) for 60 s. The resulting seed/water mixture was placed in the refrigerator at 4° C. for 24 h, after which, the supernatant was gravity filtered through blotting paper (grade 703, VWR). The filtered supernatant was frozen in plastic trays and lyophilized to produce a dried, crude extract (yield=3.8% of fresh seed weight). The crude extract was further purified by flash chromatography (3 cm×60 cm column) over Amberlite XAD7-HP resin. The extract (1.5 g in 150 mL deionized water) was applied to the column, washed with 4 column volumes of deionized water to remove sugars and other hydrophilic contaminants, and the colored fraction eluted with 2 column volumes of methanol containing 0.1% (v/v) acetic acid. The organic solvent was removed by rotary evaporation, and the water removed by lyophilization to produce a semi-pure colored extract (yield=30% of crude extract weight). This extract was analyzed by high performance liquid chromatography (HPLC) with ultraviolet/visible light (UV/VIS) detection using an HPLC system composed of two LC-20AD pumps (Shimadzu Co, Columbia, Md.), an SPD-20AV UV/Vis detector, and a Supelcosil LC18 column (4.6×150 mm, 5 µm particle size, Supelco, Bellefonte, Pa.). The mobile phase consisted of (A) 0.1% formic acid in water and (B) 0.1% formic acid in methanol. The initial mobile phase composition was 5% B. This concentration of B increased linearly over 45 min to 50% and then increased from 50% to 95% over the subsequent 5 min. After a 5 min isocratic period at 95% B, the mobile phase was returned to 5% B and allowed to re-equilibrate for 5 min. The flow-rate was 1 mL/min. The eluent was monitored at $\lambda$=280, 325, and 445 nm.

This semi-pure colored extract was subjected to preparative high performance liquid chromatography (HPLC) using an Agilent PrepStar® HPLC system equipped with a 440-LC fraction collector (Santa Clara, Calif., USA). The extract was dissolved in deionized water to a final concentration of 20 mg/mL and filtered through 0.45-µm syringe filter prior to introduction into the HPLC. Samples (10 mL) were injected and separation was achieved using a Viva C18 column (250 mm×10 mm×5 µm, Restek, Bellefonte, Pa., USA). A binary mobile phase consisting of solvent A: deionized water containing 0.1% of acetic acid and solvent B: acetonitrile was used at a flow rate of 4 mL/min. The percentage of B increased with time as follows: 0 min, 5%; 0-40 min, 5-30%; 40-45 min, 30-95%; 45-48 min, 95%; 48-49 min, 95-5%; 49-51 min 5%. The eluent was monitored at $\lambda_{max}$=445 nm. Fractions were collected at 30-s intervals (2 mL each) from 19.5 min to 26 min. The peak of interest, perseorangin, eluted at approximately 22 min. All perseorangin fractions were combined and dried under vacuum to produce "crude perseorangin".

Once dried, the "crude perseorangin" samples were diluted with deionized water and subjected to an additional round of preparative HPLC using an Ultra Aromax® 250 mm×10 mm×5 µm column (Restek, Bellefonte, Pa., USA). Samples were resolved using a binary gradient of solvent A: deionized water containing 0.1% acetic acid and solvent B: methanol at a flow rate of 4 mL/min. The percentage of B was increased as a function of time as follows: 0 min, 48%; 0-13.5 min, 48-65%, 13.5-14.5 min, 65%; 14.5-15 min, 65-4%; 15-17 min, 48%. The eluent was monitored at $\lambda_{max}$=445 nm. Fractions were collected at 24-s intervals (1.6 mL each from 8.9 min to 14.5 min). The peak of interest eluted as the later of two overlapping peaks at approximately 12 min to produce "semi-pure perseorangin."

"Semi-pure perseorangin" fractions were combined, dried, and re-dissolved in deionized water. As a final purification step, "semi-pure perseorangin" was separated on an Ultra Aromax® column (150 mm×4.6 mm×5 µm, Restek, Bellefonte, Pa., USA). A binary mobile phase of solvent A: deionized water containing 0.1% acetic acid and solvent B: methanol was employed at a flow rate of 1 mL/min. The percentage of B changed with time as follows: 0-30 min, 45%-65%; 30-32 min, 65-90%; 32-34 min, 90%; 34-35 min 90-45%; 35-37 min, 45%. The eluent was monitored at $\lambda_{max}$=320 nm and 445 nm. The peak of interest eluted at 9.5-10 min.

Untargeted Metabolomic Analysis

For metabolomics analysis, 5 biological replicates of both CASE and uncolored avocado extracts were prepared. Each replicate contained approximate 10-g portions from two avocado seeds, totaling 20 g of seed per replicate. CASE replicates were prepared by blending ~20 g of seeds into 400 mL of deionized, distilled water. For uncolored replicates ~20 g of seeds was blended into 400 mL of deionized distilled water containing tropolone (0.041 mmol). Samples were separated by reverse-phase HPLC using a Prominence® 20 UFLCXR system (Shimadzu, Columbia, Md., USA) with a Waters (Milford, Mass., USA) BEH C18 column (100 mm×2.1 mm 1.7 µm particle size) maintained at 55° C. and a 20 min aqueous acetonitrile gradient, at a flow rate of 250 µL/min. Solvent A was HPLC grade water containing 0.1% formic acid and Solvent B was HPLC grade acetonitrile containing 0.1% formic acid. The initial condition was 97% A and 3% B, increasing to 45% B at 10 min, 75% B at 12 min where it was held at 75% B until 17.5 min before returning to the initial condition. Mass spectrometry experiments were performed on a 5600 TripleTOF with a Duospray ion source (AB Sciex, Framingham, Mass., USA). The capillary voltage was set at 5.5 kV in positive ion mode and 4.5 kV in negative ion mode, with a declustering potential of 80 V. The software uses a dynamic background subtraction algorithm to determine when a new ion appears in the mass spectra during the chromatographic run so that it does not acquire MS/MS of background ions. The mass spectrometer was operated in Information Dependent Acquisition mode with a 100-ms survey scan from 100 to 1250 m/z and up to 20 MS/MS product ion scans (100 ms) per duty cycle using a collision energy of 50 V with a 20 V spread. Unsupervised PCA was conducted using MarkerView™ 1.2.1 (MDS Sciex, Ontario, Canada), which employed a covariance matrix with Pareto scaling. Known compounds were identified using the Scripps METLIN metabolomics database.

High-Resolution Mass Spectrometry (HRMS)

HRMS was performed using 5600 TripleTOF with a Duospray ion source (AB Sciex, Framingham, Mass., USA). Ionization conditions are the same as described in Section 2.3. The Formula Finder tool (AB Sciex) was used to predict the molecular formula of the compound of interest. The program uses the mass defect of the molecular ion, an estimated mass accuracy, and the "Nitrogen Rule" to calculate possible chemical formulas. The mass defect varies for different elements. For carbon it is 0.00000 for hydrogen plus 0.00783 for oxygen negative 0.00508. It also makes the assumption that the M+H ion is an even electron ion.

Attenuated Total Reflection (ATR) Fourier Transfer-Infrared Spectroscopy (FTIR)

Infrared spectra were collected using a Bruker Vertex V70 spectrometer (Bruker Optics, Billerica, Mass., USA) using a Harrick MVP Pro Star ATR accessory with a diamond crystal. All spectra were acquired between 4000 and 400 $cm^{-1}$ at 6 $cm^{-1}$ resolution by averaging 100 scans using a DLaTGS detector.

One-Dimensional (1D) NMR Experiments $^1H$ and $^{13}C$ NMR experiments were conducted on a Bruker Avance III spectrometer (Billerica, Mass., USA) equipped with a broad band observed nitrogen-cooled 5-mm probe operating at 500.20 and 125.77 MHz for $^1H$ and $^{13}C$ nuclei, respectively. All experiments were performed at 25±0.01° C., and the spectra were processed by the Bruker Topspin software package v3.2.

$^1H$ NMR spectra were recorded using the following acquisition parameters: 1 K scans and 4 dummy scans, 64 K data points, 90° pulse angle, relaxation delay 3 s to ensure quantitative results and spectral width of 12 ppm. Baseline correction was achieved by applying a polynomial fourth-order function for accurate quantitation upon integration of signals of interest. The spectra were acquired without spinning the NMR tube in order to avoid spinning side bands of the first or higher order. Chemical shifts are reported in ppm and were calibrated in reference to DMSO-$d_6$ ($\delta$=2.51 ppm).

$^{13}C$ NMR spectra were obtained with proton decoupling, using the inverse gated decoupled and the fully decoupled methods. The spectra were recorded with spectral widths of 200 ppm using 64 K data points, a 90° excitation pulse (13 s), an acquisition time of 0.8 s and relaxation delay of 8 s. Scans (4 K) were collected and spectra were zero-filled to 128 K. For all free induction decays (FID), line broadening of 1 Hz was applied prior to Fourier transform. Chemical shifts are reported in ppm from DMSO-$d_6$ ($\delta$=40).

Two-Dimensional (2D) NMR Experiments

Experimental details for the 2D NMR experiments used in this study can be found elsewhere ((Berger et al., 2004, 200 and More NMR Experiments, A Practical Course, Weinheim: Wiley-VCH; Dias et al., Analytical Methods, 2015, 7:5226-5238).

Gradient selected $^1H$-$^1H$ correlation spectroscopy (H-H-gCOSY) experiments were conducted using the following parameters: 8 dummy scans, 32 scans, 256 increments, SW of 12 ppm in F1 and F2 dimensions, 2 K data points (TD) in the F2 dimension, and a relaxation delay of 2.0 s. Zero-filling was applied to the spectra to a final size of 2 K×2 K prior to Fourier transformation.

$^1H$-$^1H$ total correlation homonuclear spectroscopy ($^1H$-$^1H$-TOCSY) spectra were acquired using the DISPI2 pulse sequence for spin lock (spin-lock time of 80 ms). The spectra were collected with 16 dummy scans, 32 scans and 512 increments, 2 K TD in the F2 dimension a SW of 12 ppm in F1 and F2 dimensions and a relaxation delay of 2.0 s. Prior to Fourier transformation linear prediction was applied to increase the data points in the second dimension to 2 K and the spectra were zero-filled to a final size of 2 K×2 K. A sine-bell squared window function was used in both dimensions.

Gradient-selected H13C heteronuclear multiple bond correlation ($^1H$-$^{13}C$ HMBC) experiment was performed with 312 increments of 2 K TD and a relaxation delay of 2.0 s. A low-pass J-filter (3.4 ms) and delays of 65 and 36 ms to observe long-range C—H couplings were used. Prior to Fourier transformation zero-filling to a 2 K×2 K matrix and π/2-shifted sine square bell multiplication was performed.

Gradient-selected $^1H$-$^{13}C$ multiplicity-edited heteronuclear single-quantum coherence (HSQC-DEPT) was conducted with 16 dummy scans, 32 scans, 128 increments and a relaxation delay of 2 s. 512×512 complex points and a spectral width of 180 ppm for $^{13}C$ (F1) and 12 ppm for $^1H$ (F2), were used. A GARP pulse train was applied during proton acquisition for carbon decoupling.

$^1H$ diffusion-ordered spectroscopy (DOSY) experiments were performed using the STE bipolar gradient pulse pair pulse sequence. 16 scans of 16 data points were collected. The maximum gradient strength produced in the z direction was 5.35 $Gmm^{-1}$. The durations of the magnetic field pulse gradients ($\delta$) and for diffusion time ($\Delta$) were 1.800 s and 100 ms respectively. The pulse gradients were incremented from 2 to 95% of the maximum gradient strength in a linear ramp.

Molecular Modeling

Molecular modeling was performed for the generation of a crude 3D structure using CHEM 3D 15.1 (ChemOffice, Perkin-Elmer, Waltham, Mass., USA) molecular mechanics; a modified version of Allinger's MM2 force field and energy minimization.

The results are now described.

HPLC-UV/Vis and LC-MS Analysis of CASE and Uncolored Avocado Seed Extracts

Figure 13A:
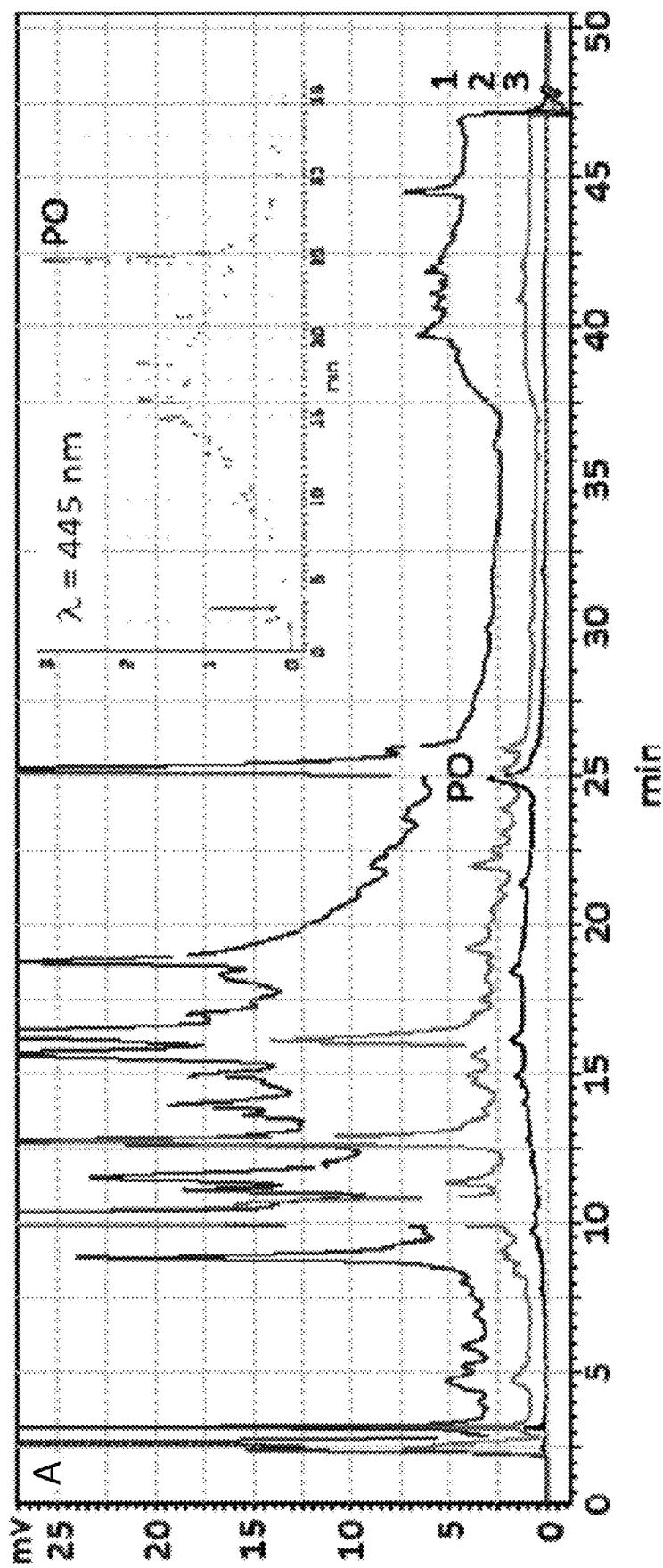
FIG. 13A and FIG. 13B, depicts HPLC-UV/Vis and untargeted LC-MS based metabolomics analysis of CASE (colored avocado seed extract) and uncolored avocado seed extract.
Figure 13B:
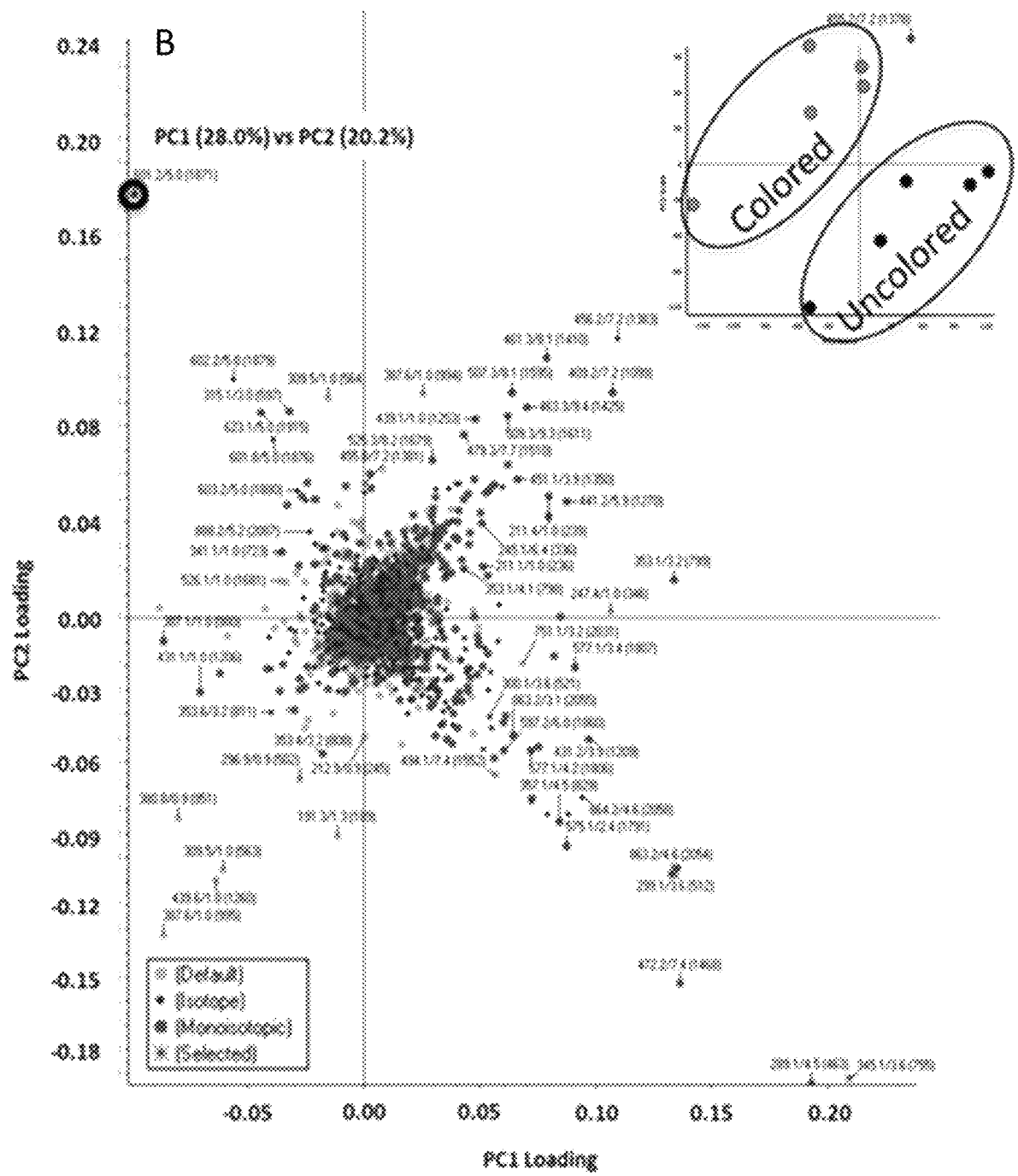
Figure 14:
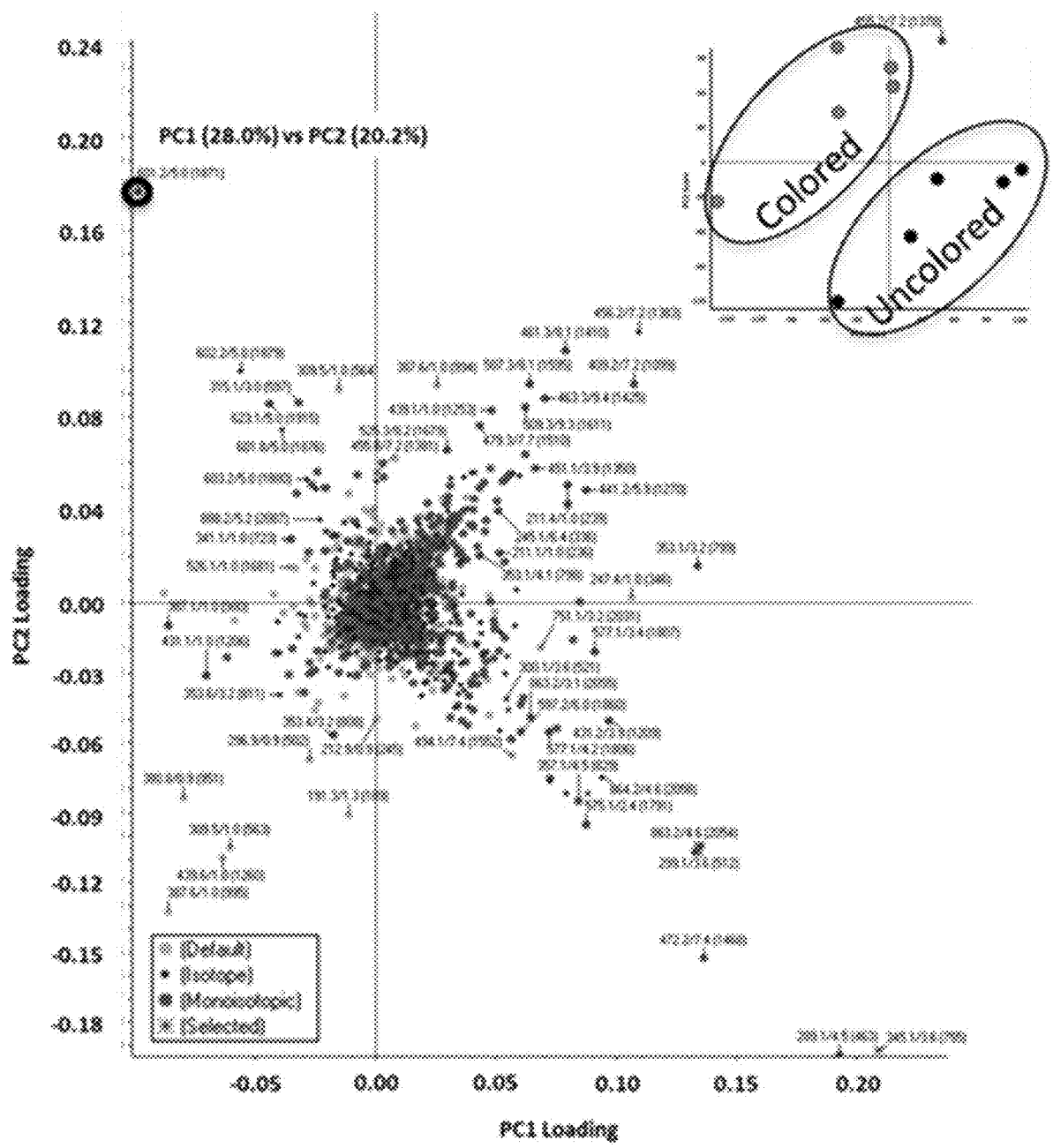
FIG. 14 depicts LC-MS metabolomics in the negative ionization modes. Principal component analysis loadings and score plots (insets) for both CASE and uncolored extract are shown.

HPLC-UV/Vis ($\lambda$=280, 325, and 445 nm) analysis showed the existence of a major peak with absorbance in the visible range (445 nm) and a retention time of 24.7 min. This peak was targeted for further purification and structure elucidation (FIG. 13A). To explore the phytochemical differences between CASE and uncolored avocado seed extracts, a mass spectrometry-based PCA approach was used. An uncolored avocado seed extract was prepared by inhibiting the action of PPO with tropolone. By comparing biological replicates of CASE and uncolored extracts, it was possible to observe compounds with masses unique to each sample. FIG. 13B shows the clustering of masses in samples analyzed in positive ion mode. Variation between samples is common when analyzing biological systems such as avocados, and that variation can be observed by the divergence distance between clustering of replicates, as seen in the PCA scores plot in FIG. 13B inset. Masses near to upper left tended to be present at higher concentrations in the CASE samples, while samples towards the lower right tended to be present at higher concentrations in the uncolored samples. The clustering of samples analyzed in negative ion mode is shown in the PCA loading plot in FIG. 14, while the corresponding score plot for replicates is shown in 14 inset. Again, masses near the upper left tended to be present at higher concentrations in the CASE samples, while samples towards the lower right tended to be present at higher concentrations in the uncolored samples. Approximately forty-nine compounds with mass unique to either the CASE or uncolored extract were observed. Among known compounds, abscisic acid and perseitol, a seven-carbon sugar alcohol, were present in both extracts, whereas epicatechin, catechin, proanthocyanidin B2, and salidroside were found only in the uncolored extract. Table 3 shows a list of compounds found to be unique to one or another of the extracts, and of particular interest was a compound with mass 603.2 in positive mode and 601.2 in negative mode identified only in the CASE.

TABLE 3

Compounds found in CASE and/or uncolored avocado seed extract by untargeted, LC-MS-based metabolomics.

| Extract | Compound | Retention time (min) | Ionization Mode | M/Z | Fragments |
|---|---|---|---|---|---|
| uncolored | no ID | 4.16 | negative | 577.1356 | 451.1055, 425.0901, 407.0788, 339.0898, 289.0725, 287.0565, 245.0819, 203.0691, 137.0238, 125.0244 |
| uncolored | no ID | 3.43 | negative | 577.1423 | 559.1265, 457.1053, 425.0921, 407.0798, 339.0899, 289.0736, 245.0829, 161.0252, 125.0248 |
| uncolored | no ID | 2.42 | negative | 863.1943 | 711.1417, 693.1323, 649.1332, 575.1234, 513.123, 449.0925, 407.0818, 297.0422, 287.0565, 243.0302, 167.0353 |
| uncolored | no ID | 6.04 | negative | 597.1882 | 477.1443, 357.1041, 345.1067, 339.0859, 315.0899, 233.0458, 209.0467, 191.0366, 167.0354, 125.0244 |
| uncolored | no ID | 7.37 | negative | 540.149 | 494.1429, 472.1618, 472.1854, 350.0873, 321.0949, 254.043, 232.0646, 212.0338, 172.0403, 144.0457, 132.0454 |
| uncolored | no ID | 5.8 | negative | 575.1223 | 539.101, 449.0882, 423.0769, 407.0779, 327.0521, 289.0725, 287.0548, 285.0419, 177.0193, 175.0397, 163.0038, 125.0247 |
| uncolored | no ID | 4.17 | positive | 601.1302 | 449.0829, 431.716, 311.0526 |
| uncolored | no ID | 7.4 | positive | 496.157 | none |
| uncolored | no ID | 4.53 | positive | 291.0866 | 207.0651, 165.0548, 161.0593 |
| uncolored | no ID | 3.67 | positive | 318.1545 | 265.1079, 247.0967, 229.0857, 147.0437, 139.0387, 123.0439, 115.0543, 111.0441, 91.0552, 77.0399, 65.0406, 55.0207 |
| uncolored | no ID | 7.4 | positive | 512.1319 | none |
| uncolored | no ID | 4.42 | positive | 865.1955 | 713.1505, 695.1389, 575.1172, 205.0844, 187.0751, 163.0598, 145.0497, 127.0387, 121.0653, 85.0299, 77.0401, 69.0351, 57.036, 53.0416 |
| uncolored | no ID | 3.8 | positive | 291.0859 | 207.0643, 179.0682, 165.0539 |
| uncolored | no ID | 3.67 | positive | 470.1613 | 399.0965, 339.0746, 320.1014, 161.0598, 147.0436, 139.0388, 123.0439, 119.0485, 115.0544, 111.0438, 91.0554, 77.0391 |
| uncolored | no ID | 4.53 | positive | 313.0674 | 279.0533 |
| uncolored | no ID | 4.64 | positive | 575.1019 | 539.098, 529.134, 279.0533, 261.0269, 251.0664, 219.0314, 201.0065, 177.0222, 170.406, 158.9965, 140.9861, 121.0652, 98.9752, 77.0406 |
| uncolored | no ID | 1.04 | positive | 365.6434 | 203.052, 185.0414 |

High-Resolution Mass Spectrometry

The isolation and purification of perseorangin from CASE was performed using multiple chromatographic steps and following the peak at 445 nm. After filtration with amberlite, which produced an extract with a higher red color intensity, the semi purified product was further purified using a preparatory C18 HPLC column.

Figure 15A:
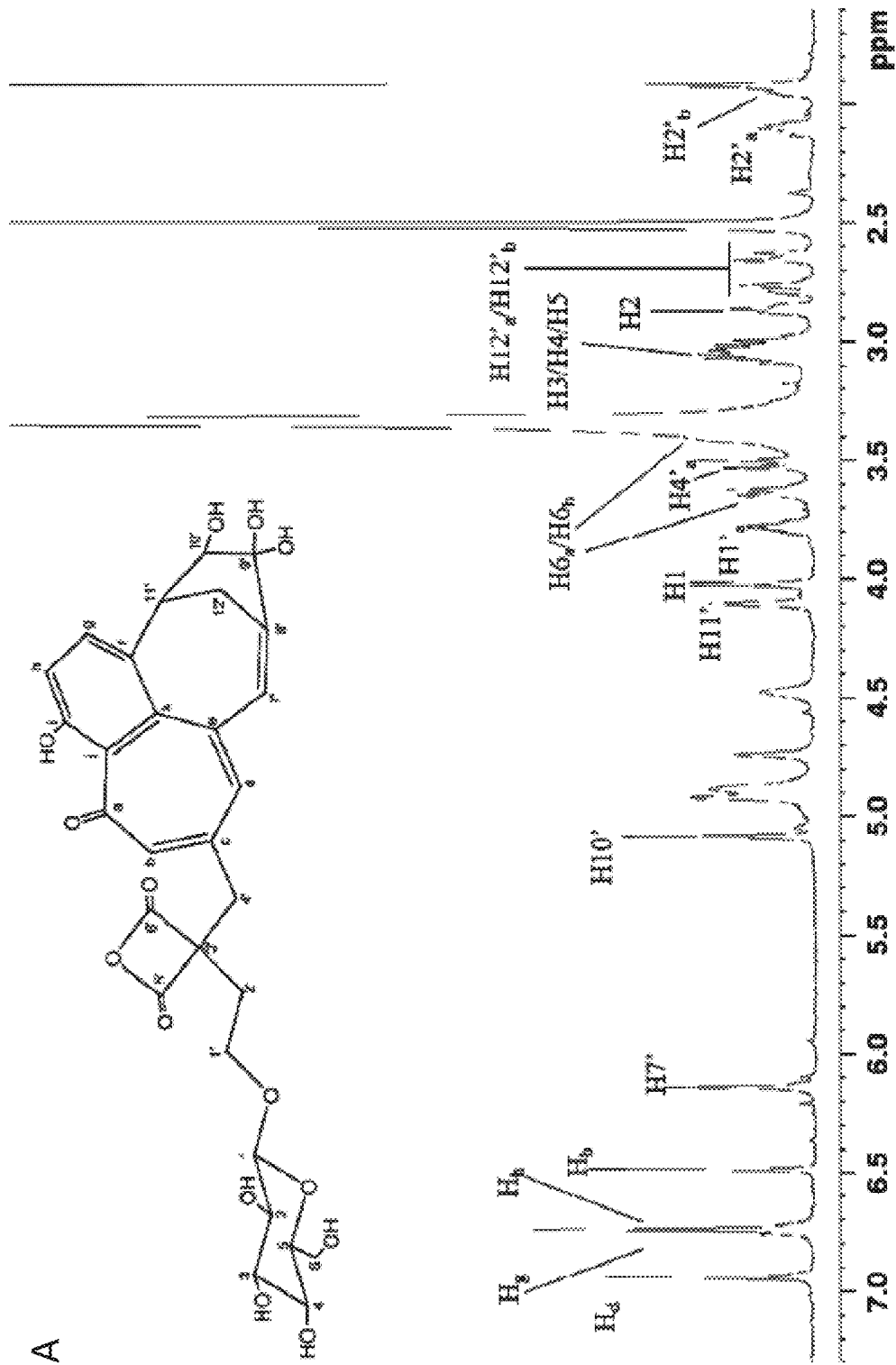
FIG. 15A and FIG. 15B, depicts the proposed chemical structure and NMR spectra of perseorangin.

The proposed chemical formula of perseorangin, as identified by NMR and HRMS, and the numbering system of the investigated molecule are presented in FIG. 15A. The purified compound collected from the Ultra Aromax column appeared as a yellow-orange solid and was analyzed via HRMS. The molecular formula of the compound was determined to be $C_{29}H_{30}O_{14}$ with an approximate mass of 602.16. It shows a main ion with m/z 603.1675 [M+1] in the positive mode and corresponds to a degree of unsaturation equal to 15. An [M+1] ion with m/z 1205 produced by the combination of two 603 units indicates the potential existence of a dimer. It is thought that the formation of a dimer is favored because of the high-energy strain of some cyclic units in the molecule, as well as the stacking between the rings of benzotropone due to π-π interactions. Further purification and structural analysis is needed to confirm the existence of the dimer and deduce its chemical structure. The MS/MS analysis also showed the presence of an abundant m/z 441.1160 fragment (Δm/z 162) indicating the presence of a hexose moiety.

IR Spectroscopy

ATR-FTIR analysis revealed a broad OH band at 3300 $cm^{-1}$ and a peak at around 1600 cm indicating the presence of C=O stretches (FIG. 5). Although imines also absorb at that wavenumber, the stoichiometric analysis showed that no nitrogen appears in the compound. In addition, benzotropolones have been previously reported to absorb at similar wavenumbers (Remias et al., 2012). Other characteristic IR frequencies appear in the spectrum include bands of the C=C in the ring at 1600-1500 cm$^{-1}$, the CH$_2$ at 1475 cm$^{-1}$, the =C—H at 3000 cm$^{-1}$ and the C—O stretching of alkyl ether groups at 1200-1275 cm$^{-1}$. The full ATR-FTIR data for purified perseorangin is as follows. IR (cm$^{-1}$): 3300, 2850, 1600, 1540, 1475, 1350, 1300, 1200, 1120, 1100, 1030, 850, 800, 650, 550, 500.

NMR Analysis

Figure 15B:
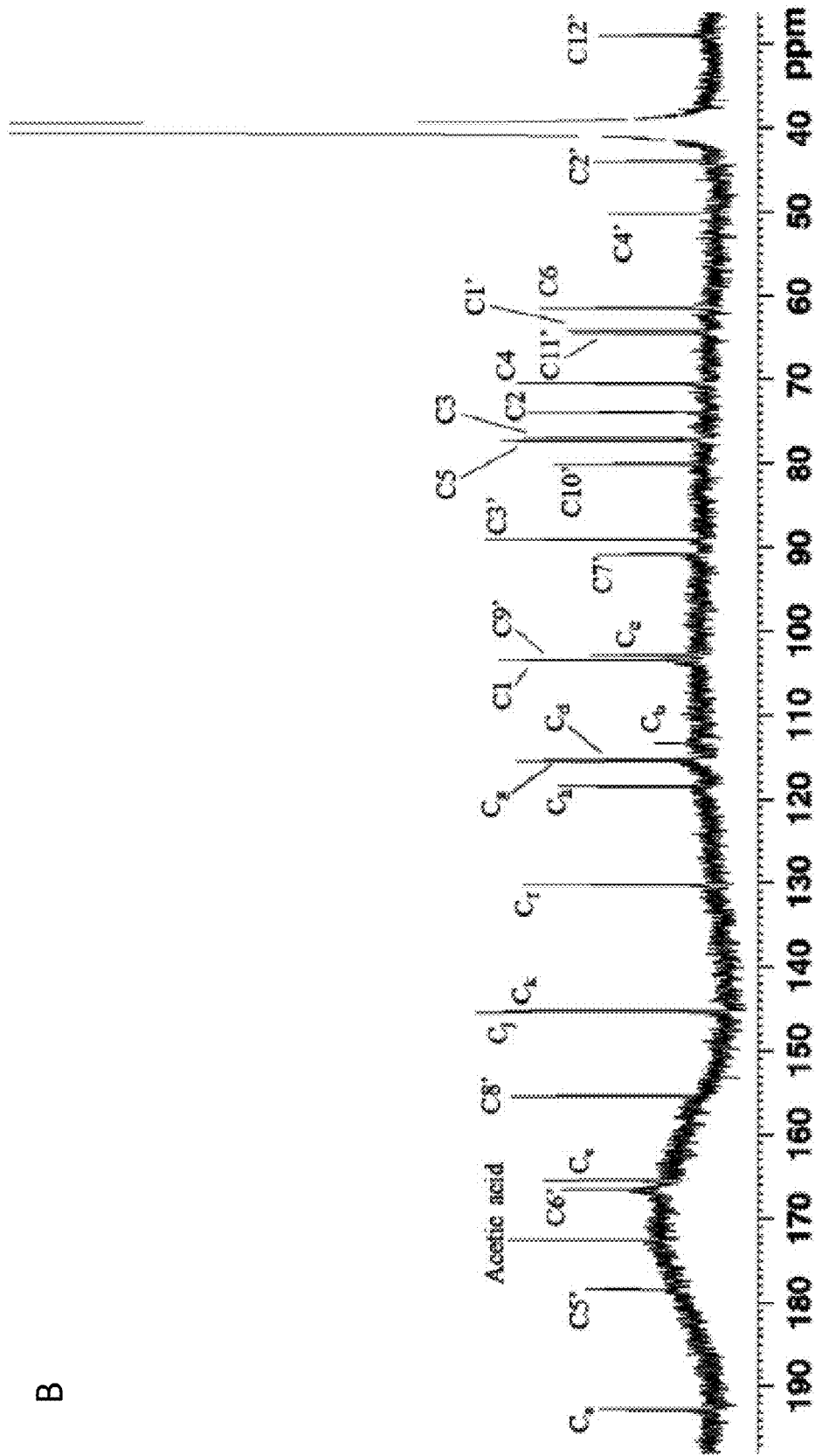

The correct $^1$H and $^{13}$C NMR assignments for the purified compound are based on the 1D and 2D NMR experiments and take into consideration factors such as chemical shifts, multiplicities due to scalar couplings and the relative integration values of various NMR signals (FIGS. 15A and 15B). Although perseorangin is soluble in water, DMSO-d$_6$ was the preferred solvent because NMR spectra with higher quality and resolution were produced. The colorant compound is a glycoside, and the starting point for the $^1$H NMR assignment was the anomeric H1 of the sugar moiety, which gives a characteristic doublet at δ 4.02 with a $^3J_{(1,2)}$ of 7.7 Hz due to coupling with H2 at δ 2.86 (FIG. 15A). This coupling constant value is characteristic of a f-D-glucopyranose ring (Remias, D. et al., FEMS Microbiology Ecology, 2012, 79:638-648) in which the angle at H1-C1-C2-H2 is about 180°. The β-glucopyranose ring conformation has reduced steric hindrance because all hydroxyl groups are equatorial and thus it is energetically favored. The COSY (FIG. 6) and TOCSY spectra (FIG. 7) allow identification of the sugar protons 3 at δ 3.07, 4 at δ 3.00, and 5 at (3.03, as well as the methylene H6a and H6$_b$ at δ 3.63 and δ 3.40 respectively, which all belong to the same spin system (FIG. 15A), and have cross peaks with each other. The chemical shifts of C1, C2, C3, C4, C5, and C6 at δ 103.33, δ 73.84, δ 76.89, δ 70.34, 677.24 and (61.45 (FIG. 15B), respectively, of glucopyranose can be easily assigned from the correlation peaks they have with the corresponding protons in the HSQC-DEPT spectrum (FIG. 8), which combines the usual one C—H bond correlation (gHSQC) together with carbon multiplicity selection similar to that obtained by the DEPT-135 experiment.

Figure 16:
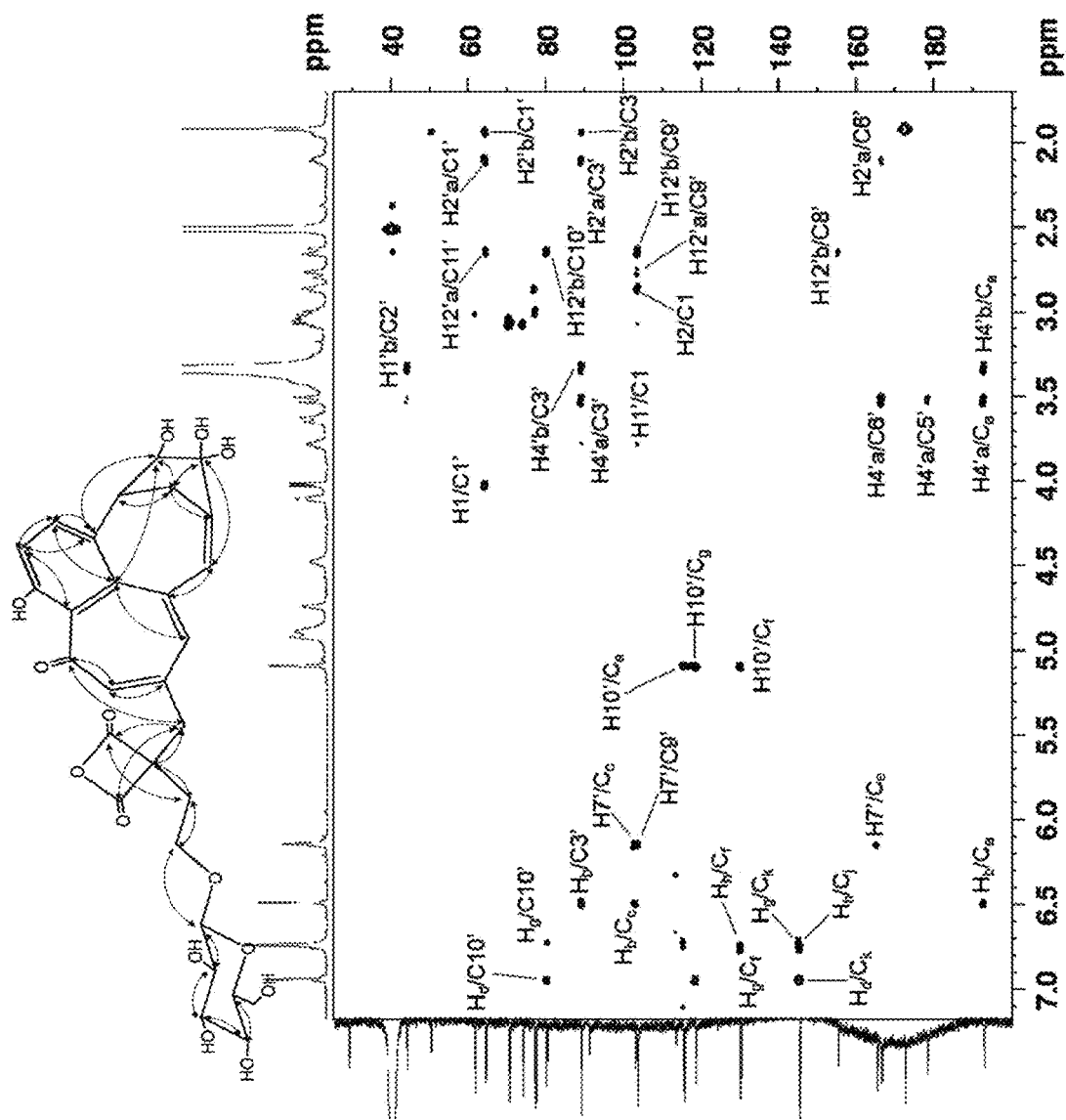
FIG. 16 depicts the $^1$H-$^{13}$C gHMBC (500 MHz) NMR analysis of perseorangin. The data was acquired over a 200 ppm spectral width in DMSO-d$_6$. Diagnostic HMBC correlations in perseorangin shown as bidirectional arrows (inset).

The sugar ring is bound to an aglycone through its anomeric carbon via an O-glycosidic bond between the oxygen atom of the anomeric carbon and the methylene C1' at δ 64.12 of a butyl group, as indicated by the correlation peaks between H1 and C1', in the HMBC spectrum (FIG. 16). The corresponding diastereotopic H1$_a$' and H1$_b$' appear at δ 3.78 and δ 3.37, respectively, as shown in the HSQC-DEPT spectrum (FIG. 8). H1$_a$' and H1$_b$' form a short spin system with the 2$_a$' and 2$_b$' methylene protons at δ 2.10 and δ 1.93, as found by their cross peaks in the COSY spectrum and the correlation peaks between C2' at δ 43.86 and H1$_a$'/H1$_b$' in the HMBC spectrum. The 2$_a$' and 2$_b$' protons have an HMBC peak with the quaternary C3' at δ 89.00. C3' has HMBC correlations with the methylene H4$_a$'/H4$_b$' at δ 3.52 and at δ 3.33, as well as an unusual four-bond correlation with a benzotropone proton, H$_b$, at δ 6.49. H2' and H4' have correlation peaks in the HMBC spectrum with a carbonyl carbon 6' at δ 166.61, whereas only the 4' protons have an HMBC signal with a second carbonyl carbon 5' at δ 178.39. H4$_a$' and H4$_b$' also have HMBC signals with another carbonyl (C$_a$) at (192.80, which is a typical chemical shift value for a benzotropolone carbonyl carbon (Lewis, J. R. et al., Phytochemistry, 1998, 49:2511-2519; Sang, S. et al., Bioorganic & Medicinal Chemistry, 2004, 12:459-467), further confirming the attachment of the aliphatic butyl chain to the benzotropone ring.

C$_a$ has an HMBC signal with H$_b$, at δ 6.49, which appears as a singlet in the 1D $^1$H NMR spectrum indicating the absence of a neighboring proton, an observation that is further confirmed by the lack of cross peaks in the COSY and TOCSY spectra. H$_d$, at δ 6.95, also appears as a singlet. However, it displays a cross peak in the TOCSY spectrum with an apparent aromatic signal at δ 6.74, which actually integrates to two protons (H$_h$ and H$_g$) at δ 6.72 and δ 6.76, respectively. Closer inspection reveals the presence of two non-symmetrical doublets characterized by a strong roof effect, where the outer lines become weaker and the inner signals become more intense. This is because of the very similar chemical shifts and the strong scalar coupling (Δδ/J<10) of H$_h$ and H$_g$ that form a strongly coupled AB spin system and generate spectra with pronounced second-order effects. The corresponding methine carbons of the benzotropone ring, C$_h$, C$_g$, C$_d$, and C$_b$, appear at δ 118.35, δ 115.41, δ 115.16 and δ 113.17, respectively, as found by the HSQC-DEPT experiment. C$_b$ has a broad signal of low intensity, which may be due to the presence of paramagnetic metals or cations that are known to reduce relaxation times (Tian, J. et al., Journal of Magnetic Resonance, 2002, 159:137-144); avocado seeds have been shown to contain considerable concentrations of C$_a$ and Mg (Witney, G. W. et al., Scientia Horticulturae, 1990, 44:279-291). The resulting short T$_2$ relaxation times may be the reason that quaternary C$_i$ could not be identified, v.i. Quaternary C$_c$, C$_j$, C$_k$, and C$_f$ appear at δ 102.77, δ 145.39, δ 145.40, and δ 130.12 as found in the HMBC spectrum.

Figure 7:
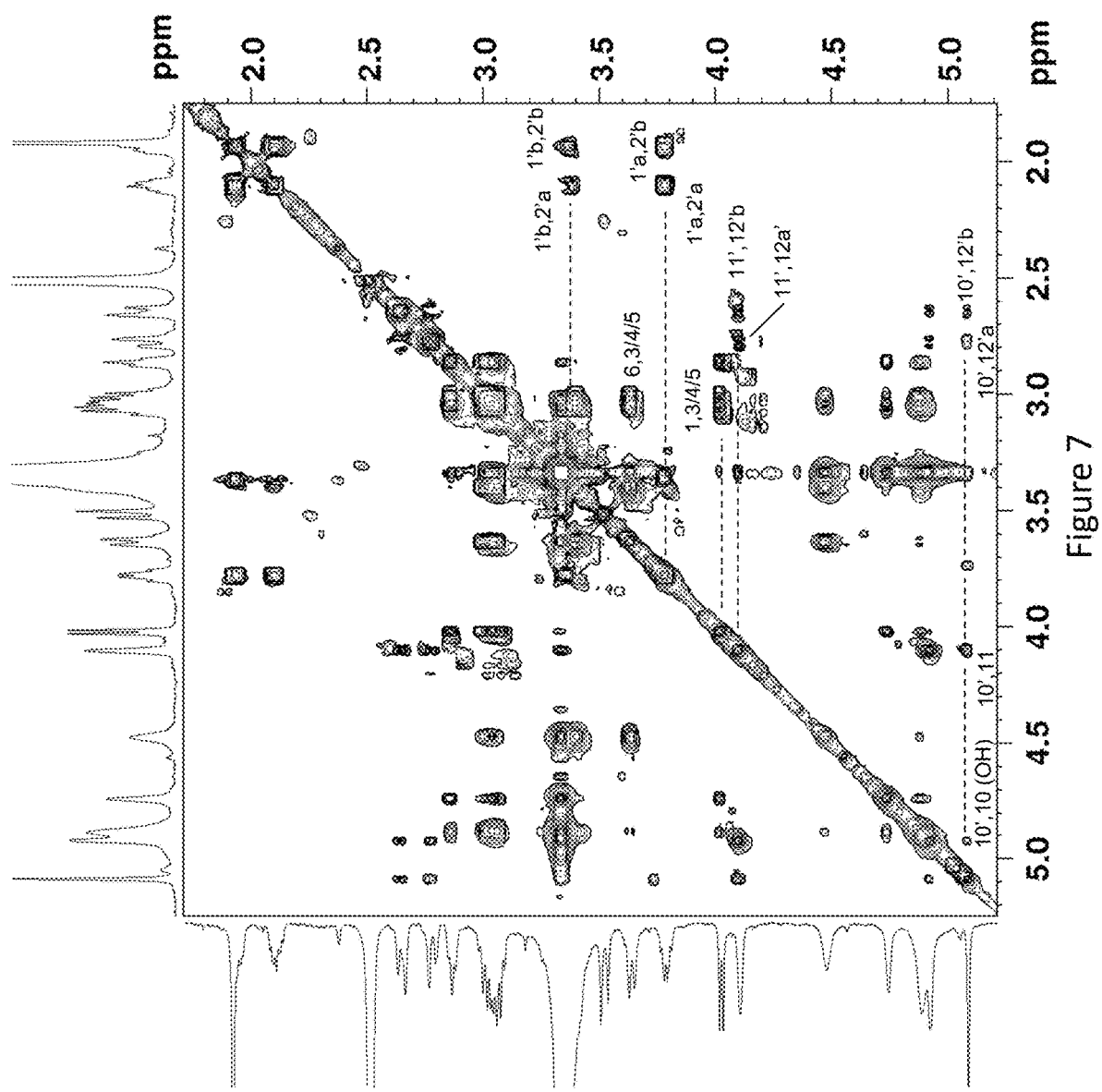
FIG. 7 depicts the $^1$H-$^1$H-TOCSY spectrum of perseorangin.

C$_g$ and C$_f$ have cross peaks in the HMBC spectrum with methine H10', at δ 5.08, indicating the attachment of a side chain in a position para relative to the —OH group of C$_i$ of the benzotropone ring. The C$_i$ v.s. could not be identified; however, it is believed that it overlaps with C6' because its signal is associated with an integral that corresponds to more than one carbon, as found by a semi-quantitative inverse-gated decoupling $^{13}$C experiment. H10' forms a 4-spin system with H11', at 64.10, and H12$_a$'/H12$_b$' at δ 2.77/2.64 as indicated by their cross peaks in the TOCSY spectrum (FIG. 7). Because the NMR experiments were run in DMSO-d$_6$, cross peaks between exchangeable protons, such as the OH proton of C10' at δ 4.92 and aliphatic protons such as 10' and 12$_a$'/12$_b$' are also visible in the TOCSY spectrum. Chemical shifts of the corresponding C10', C11', and C12' at δ 80.00, δ 64.39, and δ 28.94, respectively, can be easily assigned by the HSQC-DEPT spectrum. Further confirmation for the para regiochemistry arises from the strong $^3$J correlation peaks in the HMBC spectrum of protons H$_g$ and H$_d$ of benzotropone with C$_k$ at 145.4 ppm.

H12'$_{ab}$ have HMBC signals with the quaternary C9' at δ 103.30, which bears two hydroxyl groups and thus appears downfield. In addition, H12$_b$' has a correlation peak in the HMBC spectrum with the quaternary olefinic C8' at δ 155.50. The olefinic H7' appears at δ 6.14 and is directly attached to C7' at δ 90.85 as found in the HSQC-DEPT spectrum. The chemical shift of C7' is relatively unusual for an olefinic carbon, in terms that appears up-field, however similar shielding effects have been previously reported for benzotropolones (Klostermeyer, D. et al., European Journal of Organic Chemistry, 2000, 13:603-609). H7' has also an HMBC correlations with C9', C$_c$, and C$_d$. The $^1$H and $^{13}$C chemical shifts of the compound are given in Table 2. FIG. 16 shows the key diagnostic correlations in perseorangin, which indicate the connectivity between various units. Further evidence arises from the DOSY spectrum (FIG. 11), which confirms the presence of one molecule as all peaks are aligned on the same diffusion coefficient value. FIG. 12 shows the 3D representation of the molecule as determined by molecular mechanics (MM2) force field calculations having as starting point a crude model structure and gradually converted to a 3D conformation by energy minimization.

Perseorangin proved to be a stable molecule even over a variety of light and temperature conditions (Shegog, 2015, Characterization of Perseorangin a Natural Orange Pigment found in Hass Avocado (*Persea americana*) Seed and its Uses as a Natural Food Colorant, PhD Thesis, The Pennsylvania State University). This is probably due to its aromaticity as the benzotropone unit can be considered as a ten-electron aromatic system. The septa-trienone moiety of benzotropone is already close to an aromatic system (6 π-electrons) due to the partial positive charge on $C_a$. The triene can close its cyclic conjugation by interacting the triene π-electron density with the in-phase and empty C=O π-antibonding orbital. The hydrogen-bonding interaction with the OH group would further decrease the energy level of the C=O π-antibonding orbital, making the antibonding orbital even more energetically accessible to the triene and thus enhancing the aromaticity even further. Despite the high energy strain of the five-membered ring at the position of carbon C8', which disrupts the planarity of the seven-membered ring, as shown by MM2 calculations, the compound seems to be aromatic, as indicated by its stability and the chemical shifts of $H_b$ and $H_d$. The formation of the dimer, which is consistently detected in MS, may occur through the breaking of the strained double bond of C8' of the five-membered ring or of the cyclopropyl ether ring. The detection of a compound with m/z 603.1687 that may correspond to an ion-radical of perseorangin, which forms during ionization in the mass spectrometer may indicate the formation of the dimer through a radical mechanism, and suggests that it could be an artifact of analysis. Further experiments are required to definitively show the existence of the dimer.

Perseorangin appears as an orange-yellow solid. It is characterized by extensive conjugation since 14 π-electrons from C=C and C=O bonds are involved in the conjugation. In addition, the lone-pair of electrons from the hydroxyl group on $C_i$ could also participate in the conjugation and form a 16 π-electron system. This extensive conjugation is responsible for a low HOMO-LUMO gap, causing a bathochromic shift that explains the orange-yellow color of the compound.

Although CASE contains several compounds that may contribute to its final color, perseorangin, a novel benzotropone-containing compound, is the most abundant component as determined by HPLC-UV/Vis ($\lambda_{max}$=445 nm). Structural information about the new compound was obtained using a variety of chromatographic and spectroscopic techniques. Further studies are needed to characterize the utility of this compound as a food color additive derived from naturally occurring reactions and to identify its biosynthetic precursors and potential natural derivatives.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

3. The edible material of claim 1, wherein the compound of general formula (2) is selected from the group consisting of
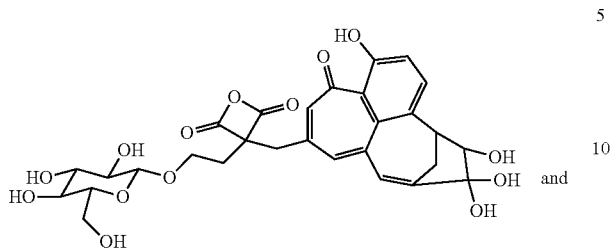
and
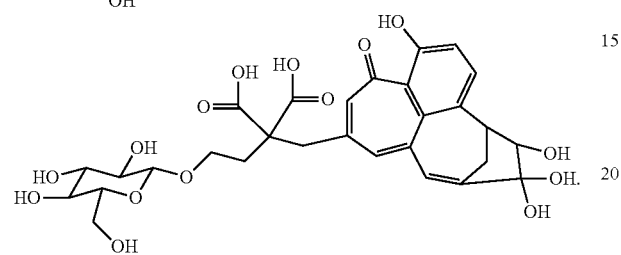

What is claimed is:

1. An edible material comprising an isolated, stable compound of general formula (2) or a salt thereof:

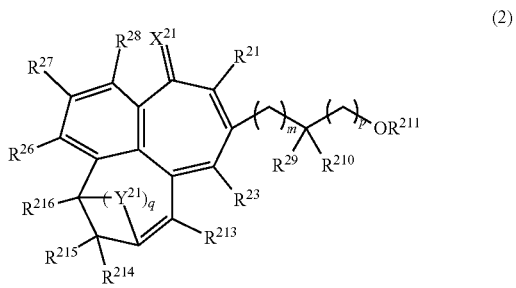

(2)

wherein in general formula (2), $R^{21}$, $R^{23}$, $R^{26}$-$R^{28}$, and $R^{213}$-$R^{216}$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein any of $R^{21}$, $R^{23}$, $R^{26}$-$R^{28}$, and $R^{213}$-$R^{216}$ are optionally joined to form a ring, wherein the ring is optionally substituted;

$R^{29}$ and $R^{210}$ are each independently selected from the group consisting of hydrogen, an alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, and C(=O)$R^{211}$, wherein $R^{29}$ and $R^{210}$ are optionally joined to form a ring;

each occurrence $R^{211}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

Y is selected from the group consisting of C($R^{217}R^{18}$), NR$^{217}$, SR$^{217}$, and OR$^{217}$;

$R^{217}$ and $R^{218}$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, halogen, and hydroxyl;

m is an integer from 0 to 11;

p is an integer from 0 to 5;

q is an integer from 1 to 5; and $X^{21}$ is selected from the group consisting of O, NH, and S;

wherein the edible material is a beverage, and wherein the isolated, stable compound of general formula (2) or salt thereof imparts a color to the beverage; and, wherein the compound of general formula (2) is present in a concentration between 0.25 mg/ml and 10 mg/ml in the edible material.

2. The edible material of claim 1, wherein the edible material has a hue selected from the group consisting of orange, red, and yellow.